US012669490B2

(12) United States Patent
Shields et al.

(10) Patent No.: US 12,669,490 B2
(45) Date of Patent: Jun. 30, 2026

(54) WATER MONITORING SYSTEM USING AN OPTIMIZED CIRCULAR FLUID FLOW PATH

(71) Applicant: AMANO TECHNOLOGIES INC., Provo, UT (US)

(72) Inventors: Derek Shields, Provo, UT (US); Dennis Olsen, Eagle Mountain, UT (US); Jason Brinton, Millcreek, UT (US); Jacob Greenwood, Orem, UT (US); Jaxon Smith, Lee's Summit, MO (US)

(73) Assignee: Amano Technologies, Inc., Provo, UT (US)

( * ) Notice: Subject to any disclaimer, the term of this patent is extended or adjusted under 35 U.S.C. 154(b) by 904 days.

(21) Appl. No.: 17/751,183

(22) Filed: May 23, 2022

(65) Prior Publication Data

US 2023/0102493 A1      Mar. 30, 2023

Related U.S. Application Data

(60) Provisional application No. 63/246,720, filed on Sep. 21, 2021.

(51) Int. Cl.
*G01N 33/18*      (2006.01)
*G01N 21/31*      (2006.01)

(52) U.S. Cl.
CPC ......... *G01N 33/1893* (2013.01); *G01N 21/31* (2013.01)

(58) Field of Classification Search
None
See application file for complete search history.

(56) References Cited

U.S. PATENT DOCUMENTS

| | | | |
|---|---|---|---|
| 5,983,734 A | 11/1999 | Mathur et al. | |
| 6,113,858 A | 9/2000 | Tang et al. | |
| 6,625,824 B1 * | 9/2003 | Lutz ......................... | E04H 4/12 |
| | | | 137/625.21 |
| 7,220,383 B2 | 5/2007 | Anderson et al. | |
| 7,544,289 B2 | 6/2009 | Straka et al. | |
| 8,360,737 B2 | 1/2013 | Smisson, III et al. | |
| 8,748,191 B2 | 6/2014 | Kraus et al. | |
| 9,034,193 B2 | 5/2015 | Shalon | |
| 9,569,858 B2 | 2/2017 | Babcock et al. | |

(Continued)

FOREIGN PATENT DOCUMENTS

| | | |
|---|---|---|
| CN | 101887064 A | 11/2010 |
| CN | 102147373 | 8/2011 |

(Continued)

*Primary Examiner* — Daniel S Larkin
(74) *Attorney, Agent, or Firm* — Morriss O'Bryant Compagni Cannon, PLLC

(57) ABSTRACT

The present invention is a system and method for automated testing, treatment, and maintenance of fluid, such as water disposed in swimming pools, spas, and other bodies of water, wherein the water testing system includes control over the amount of reagent used in testing, and the frequency of testing of any measurable aspect of the test water, wherein the system reduces power consumption and eliminates components found in prior art systems for testing and flushing of test water mixed with reagents from a testing reservoir using a fluid flow path system.

18 Claims, 18 Drawing Sheets

(56) References Cited

U.S. PATENT DOCUMENTS

| | | | |
|---|---|---|---|
| 9,776,888 B1 * | 10/2017 | Kurani | C02F 1/66 |
| 10,150,680 B1 | 12/2018 | Kurani et al. | |
| 10,287,180 B1 | 5/2019 | Kurani et al. | |
| 10,379,132 B1 | 8/2019 | Wiederin et al. | |
| 10,577,256 B1 | 3/2020 | Kurani et al. | |
| 10,604,954 B2 | 3/2020 | Shalon et al. | |
| 10,737,951 B2 | 8/2020 | Miller et al. | |
| 10,865,097 B2 | 12/2020 | Kraus et al. | |
| 2017/0092096 A1 | 3/2017 | Fernandes et al. | |
| 2018/0112430 A1 | 4/2018 | Shalon et al. | |
| 2019/0003976 A1 | 1/2019 | Clark | |
| 2019/0084753 A1 | 3/2019 | Hartmann | |
| 2020/0271635 A1 * | 8/2020 | Key | G01K 3/005 |
| 2020/0362846 A1 * | 11/2020 | Mar | F04B 43/046 |
| 2021/0146367 A1 | 5/2021 | Szpak et al. | |
| 2021/0188672 A1 | 6/2021 | Shalon et al. | |
| 2022/0137021 A1 * | 5/2022 | Zima | G01N 33/18 |
| | | | 436/165 |

FOREIGN PATENT DOCUMENTS

| | | | | |
|---|---|---|---|---|
| CN | 101825559 B | * | 1/2012 | |
| CN | 204694624 U | * | 10/2015 | |
| CN | 204694702 U | * | 10/2015 | |
| CN | 105675354 A | | 6/2016 | |
| CN | 205483680 | | 8/2016 | |
| CN | 207198137 U | * | 4/2018 | |
| WO | WO-2020180285 A1 | * | 9/2020 | G01N 21/78 |

* cited by examiner

100

105

110

115

750

800

805

900

115

905

WATER MONITORING SYSTEM USING AN OPTIMIZED CIRCULAR FLUID FLOW PATH

BACKGROUND

Field of the Invention: This invention relates generally to fluid testing devices. More specifically, the system is a fluid monitoring system, such as for water, which is capable of taking multiple automated measurements of the quality of the fluid so that appropriate action can be taken to treat the fluid depending on the results of the measurements.

Description of Related Art: There is a need for testing of fluids so that they are safe for recreation or consumption. Throughout this document, water may be used as an example of a fluid that may be tested, but it should be understood that any fluid may be tested using the system and method of the present invention. For example, pools and spas need regular, if not daily testing, to ensure the quality of the water. Water quality may refer to the chemical, physical, and biological characteristics of water based on the standards of its usage. It is most frequently used by reference to a set of standards against which compliance, generally achieved through treatment of the water, can be assessed. Because many bodies of water are outdoors or are used by many people, water quality may change rapidly and may have undesirable results for those who enter the water if the water is unsafe or unsanitary.

Other bodies of water that are not found within a strictly controlled environment may also require regular testing. These bodies of water may include ponds, lakes, reservoirs, streams, and rivers. Whatever the nature of the body of water, there are quality standards that must be met for recreational, agriculture, wastewater, potable water, and other uses.

Given the large number of pools, spas and other bodies of water that require regular monitoring of water quality, there is an industry devoted to water testing. Unfortunately, most water testing is done manually. Manual testing is typically not performed as often as it should, and the results may be affected by many variables in the testing process. These variables may include but should not be considered as limited to temperature at time of reading, size of drop test, inability to accurately detect changes in color with the naked eye, etc.

The prior art contains various systems for water quality testing. In one example, a water monitoring device is submerged directly into the test water (i.e., the water that is being tested and monitored). In another example, the water monitoring device floats in the test water or is at least partially submerged. Additionally, another water monitoring device is externally attached to a water containment structure or to one of many different water modification systems using a fitting (e.g., a tee fitting) and/or flexible tubing.

In some examples, the water monitoring device comprises a housing, a replaceable cartridge, a testing reservoir, a driver, and a colorimeter. The device may also include a computing system, battery, and communication system, such as a Bluetooth transceiver.

In some examples, the replaceable cartridge contains one or more testing strips. In one example, the testing strips are housed in a waterproof, leak-proof container. The testing strips may be wrapped around a reel within the housing. The testing strips are then partially unwound to expose a pocket.

In one example, the testing strip contains a row of pockets filled with reagents. During testing, the water monitoring device opens one or more pockets to release the reagents into the testing water. Once the chemical strip has no more reagents, the entire cartridge is replaced.

To perform a test, the water monitoring device delivers some test water into a testing reservoir and adds one or more reagents to it. To add the reagent into the testing reservoir, the strip is partially unwound to expose a pocket and dispense reagent from the exposed pocket. The test water and reagents are then mixed. A colorimeter is then used to determine the color of the mixture. The color may then be compared to a table of known values to determine the chemical levels in the test water.

Once the water-reagent mixture has been analyzed, the testing reservoir flushes the mixture from the testing reservoir and pulls more test water into the testing reservoir in preparation for the next test. Thus, the water monitoring device may automatically run a series of tests.

It is known that there are some automated systems for monitoring water quality and there are even some water monitoring systems that float in the bodies of water and are battery powered. The longer a battery can last, the longer the automated monitoring process can continue. Thus, automated systems must be made to operate in a manner that enables the least expenditure of power to perform its function. Other water testing systems require regular maintenance because of the complexity of the device. Accordingly, it would be an advantage over the prior art to reduce power consumption and complexity in an automated and battery-operated water monitoring system in order to extend the time in which water monitoring can be performed without having to replace or recharge a battery or perform maintenance.

BRIEF SUMMARY

The present invention is a system and method for automated testing, treatment, and maintenance of fluid, such as water disposed in swimming pools, spas, and other bodies of water, wherein the water testing system includes precise control over the amount of reagent used in testing, and the frequency of testing of any measurable aspect of the test water, wherein the system is optimized for minimal power consumption and reduced complexity of a system for optimized testing and flushing of test water mixed with reagents from a testing reservoir using a fluid flow path system, and the use of fewer moving parts in the fluid flow path to reduce failure and increase the usable life of the water testing system.

In a first aspect of the invention, it should be understood that the bodies of water that may be tested may include but should not be considered as limited to aquaculture, aquariums, rivers, lakes, ponds, streams, wells, cooling towers, waste treatment systems, pools, hot tubs, etc.

These and other embodiments of the present invention will become apparent to those skilled in the art from a consideration of the following detailed description taken in combination with the accompanying drawings.

DETAILED DESCRIPTION

Figure 1:
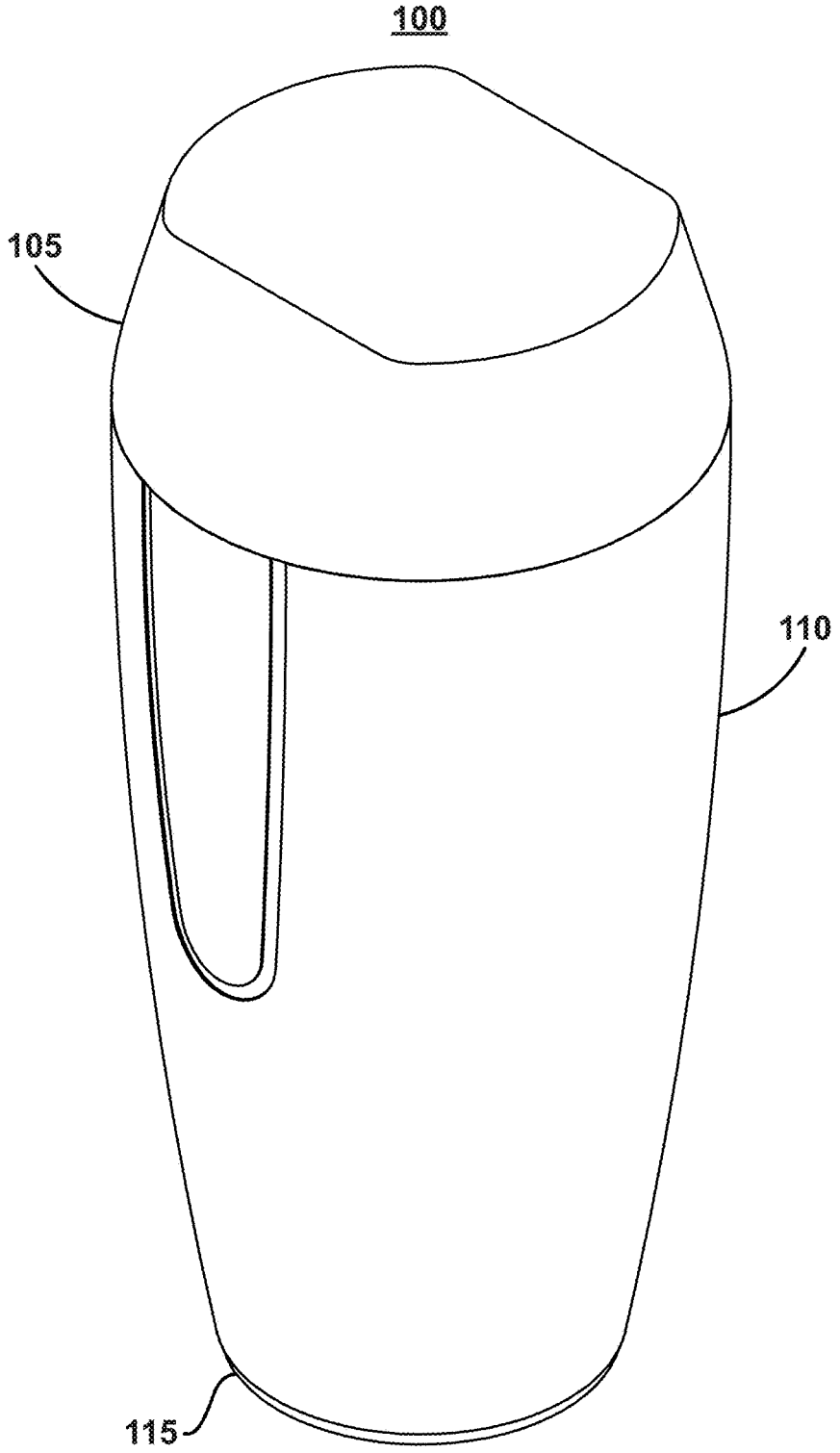
FIG. 1 illustrates a perspective view of an example of the fluid monitoring device.

Reference will now be made to the drawings in which the various embodiments of the present invention will be discussed so as to enable one skilled in the art to make and use the invention. It is to be understood that the following description illustrates embodiments of the present invention and should not be viewed as narrowing the claims which follow.

Furthermore, it is to be understood that this disclosure is not limited to the parameters of the particularly exemplified systems, methods, apparatus, products, and processes, which may, of course, vary. Thus, while certain examples of the present disclosure will be described in detail, with reference to specific configurations, parameters, components, elements, etc., the descriptions are illustrative and are not to be construed as limiting the scope of the claimed invention. In addition, the terminology used herein is for the purpose of describing the examples and is not necessarily intended to limit the scope of the claimed invention.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

The following document describes a fluid monitoring device that monitors the chemical levels of a fluid through periodic testing. The following examples are addressed to the fluid being water. However, it should be understood that any fluid may be tested using the embodiments of the invention and that the examples and claims should not be considered as limited to just water.

As just one example of the use of the fluid monitoring device, it may be used to automatically measure multiple parameters of water such as the chlorine, pH, and alkalinity levels. It should be understood that any chemical test may be performed on a fluid where the required reagent may be stored in the cartridges of the present invention. The reagent may be a substance or compound added to a system to cause a chemical reaction or added to test if a reaction occurs. The fluid monitoring device may also transfer a chemical level data to a user's phone, tablet, computer or other computing device that has access to a network via a wired or wireless connection. Additionally, the water monitoring device may send alerts to a user if any of the chemical levels are outside of a predefined range.

Figure 2:
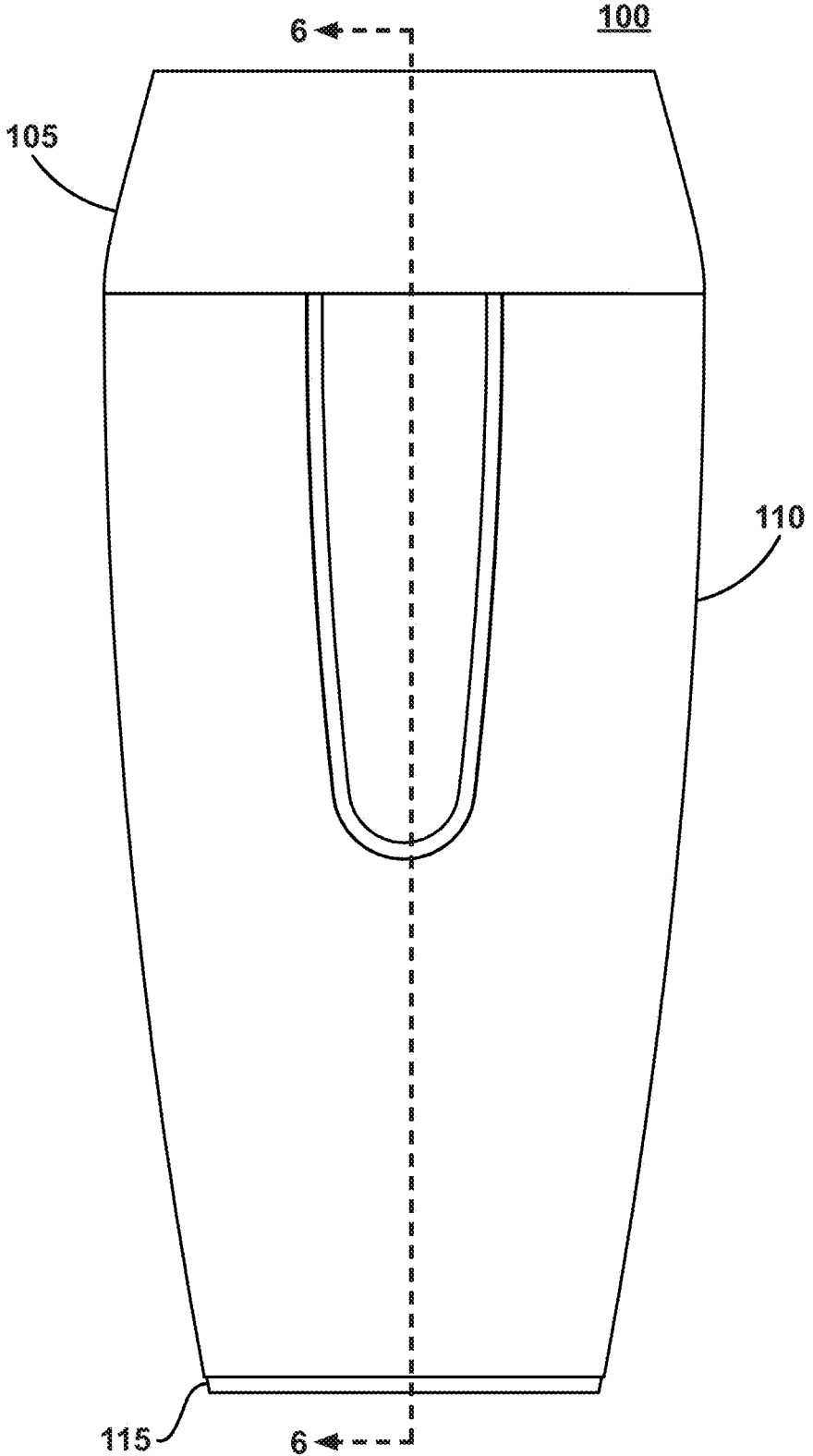
FIG. 2 illustrates a front view of the fluid monitoring device of FIG. 1.
Figure 3:
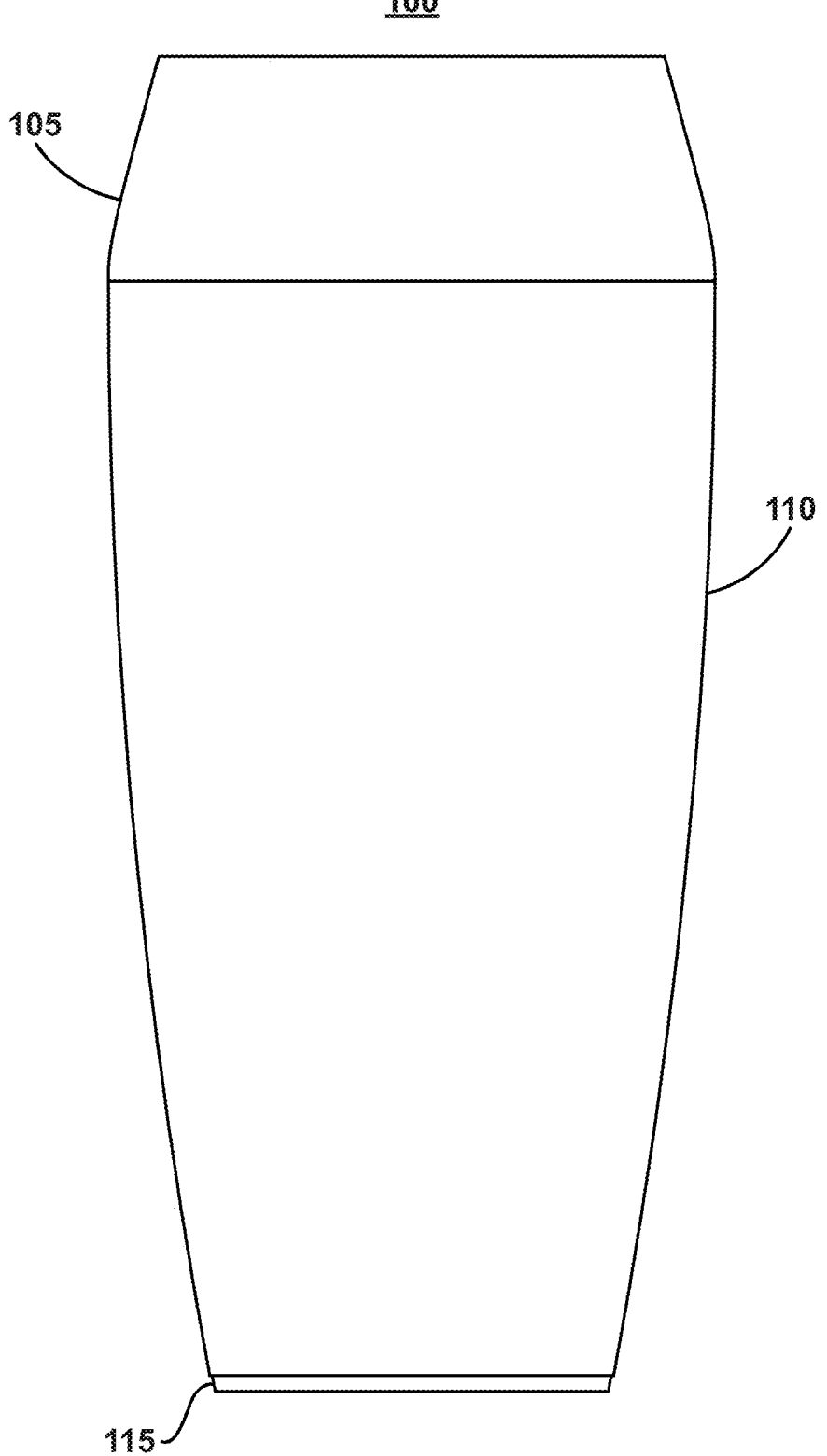
FIG. 3 illustrates a back view of the fluid monitoring device of FIG. 1.

FIGS. 1-3 illustrate different views of an example of a water monitoring device 100. In some examples, the water monitoring device 100 includes a lid 105, a body 110, and a bottom cap 115. In some examples, the lid 105 and the body 110 thread together (e.g., the lid 105 has male threads and the body 110 has matching female threads) and create a waterproof and dust-resistant seal. The waterproof seal protects the internal components (e.g., the computing system and the battery) from water and dust damage. Additionally, in some examples, some of the internal components of the water monitoring device 100 have individual waterproof and dust resistant cases (not shown). Thus, in some examples, the water monitoring device 100 will not be damaged even if water enters the body 110.

It is noted that the bottom cap 115 may not be needed, and thus may be replaced with a bottom plate that does not include any apertures therethrough.

In some examples, the body 110 is a cylinder that is tapered on both ends. However, the shape of the body 110 may vary to accommodate different needs and preferences. For example, in some examples, the body is a square prism, a triangular prism, or any type of regular or irregular prism. Additionally, in some examples the body is only tapered on one end or on neither end.

In some examples, the water monitoring device 100 is made of plastic. For example, the water monitoring device 100 may be made of a thermoplastic or thermoset plastic. In other examples, the water monitoring device 100 is made of a metal, such as aluminum, steel, stainless steel, or copper.

In some examples, the metal is treated with a rust-resistant coating. The water monitoring device 100 may also be treated with a UV-resistant coating.

Figure 4A:
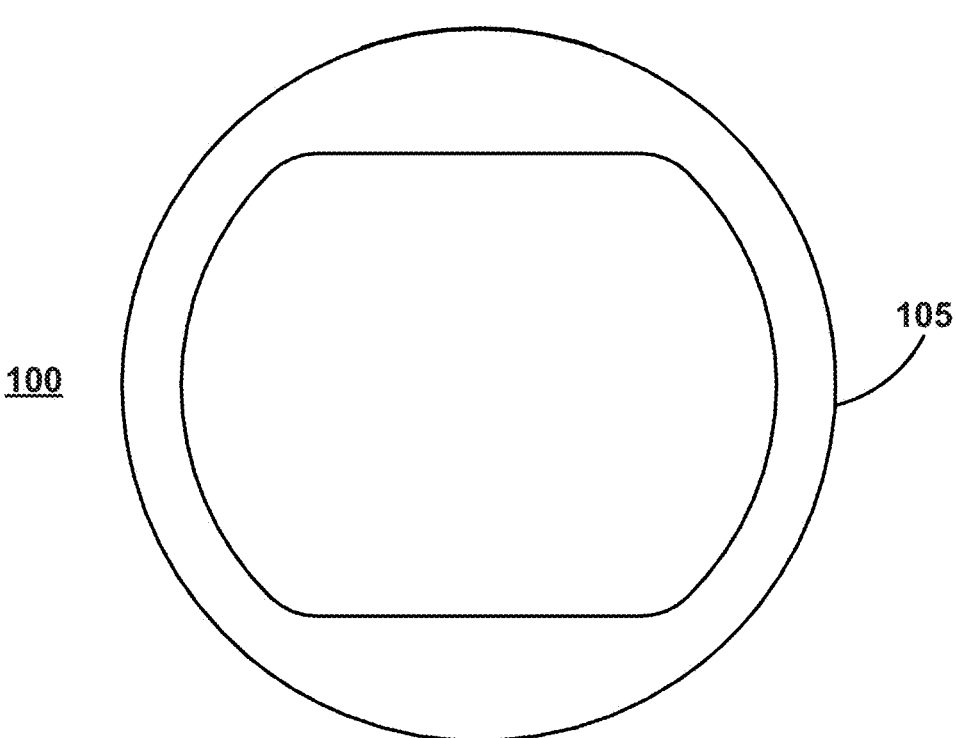
FIG. 4A illustrates a top view of the fluid monitoring device of FIG. 1.
Figure 4B:
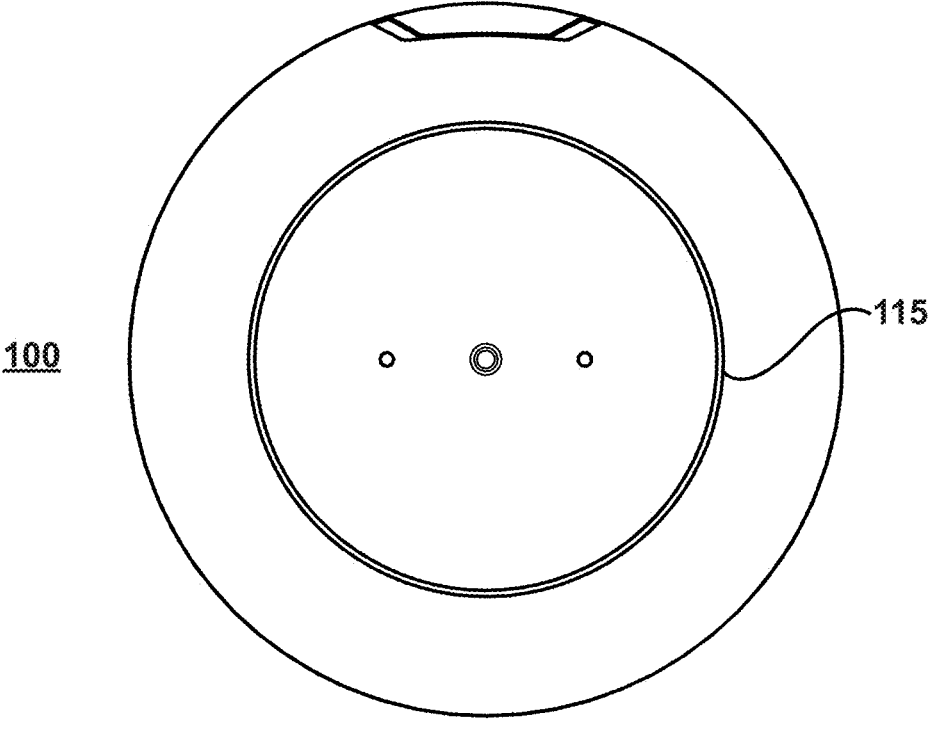
FIG. 4B illustrates a bottom view of the fluid monitoring device of FIG. 1.

FIGS. 4A and 4B illustrate a top and bottom view respectively of the water monitoring device 100. Both the lid 105 and the bottom cap 115 may be easily removed. When the lid 105 is removed, the internal components of the water monitoring device 100 may be accessed. Additionally, when the bottom cap 115 is removed, the water monitoring device 100 may be modified to be compatible with different water systems.

Figure 5:
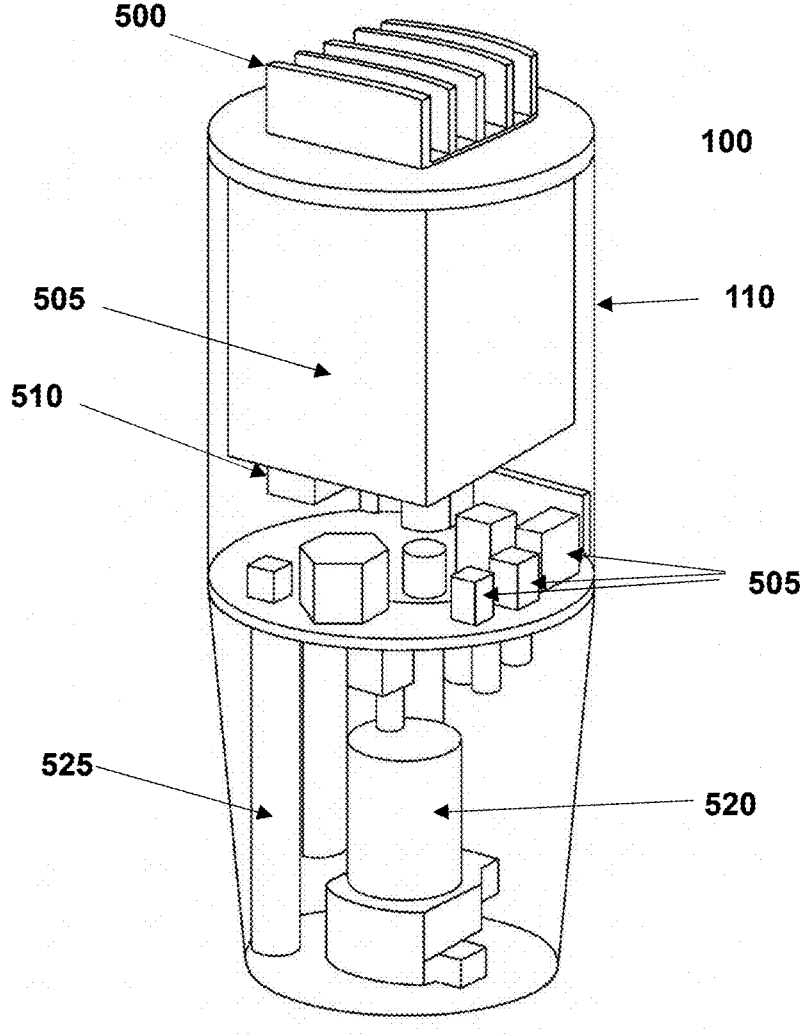
FIG. 5 illustrates a partially transparent view of the fluid monitoring device of FIG. 1.

FIG. 5 illustrates a transparent view of the water monitoring device 100. In an example and as shown, the water monitoring device 100 may be comprised of a body 110, a plurality of reagent pouches 500, a reagent cartridge 505, a control board 510, a plurality of individual reagent pumps 515, a mixing pump 520, and a battery 525. Multiple reagent pouches 500 may be housed within the reagent cartridge 505. The plurality of reagent pouches 500 are consumables and may be easily replaced. Not shown is a testing reservoir that is also disposed within the body 110, various fluid flow tubes, color sensors, and valves. It is generally the case that the plurality of reagent pouches 500 may contain any number of reagents. Thus, some reagents may be found in more than one of the pouches 500 while other reagents might only be found in a single one of the plurality of reagent pouches. The user may put any desired number of reagents in the plurality of reagent pouches 500. The user may decide to put more than one pouch of a particular reagent in the pouches if the particular reagent might be used more often or a larger quantity of the reagent might be used for particular tests.

For assembly, the reagent pouches 500 may snap into place when they are inserted into slots of the reagent cartridge 505. In an example, the reagent pouches 500 may have tabs/slots (not shown) that snap into tabs/slots (not shown) on the reagent cartridge 505. The reagent pouches 500 may be removed by pulling upward on them. A user may therefore easily remove and insert the individual reagent pouches 500 within the reagent cartridge 505. In an example, the reagent pouches 500 may be coupled to a circular fluid flow path. Additionally, in some examples, the reagent pouches 500 are held in place by the lid 105. More specifically, the lid 105 pushes down on the reagent pouches 500 in the reagent cartridge 505 when it is inserted into the body 110.

In alternative embodiments, the entire reagent cartridge 505 may be removed from the water monitoring device 100. The reagent pouches 500 that need replacing are then removed and replaced with a new reagent pouch, or all of the reagent pouches 500 are removed as a single unit and replaced at the same time. Then, the reagent cartridge 505 is reinserted into the body 110 of the water monitoring device 100.

Figure 6:
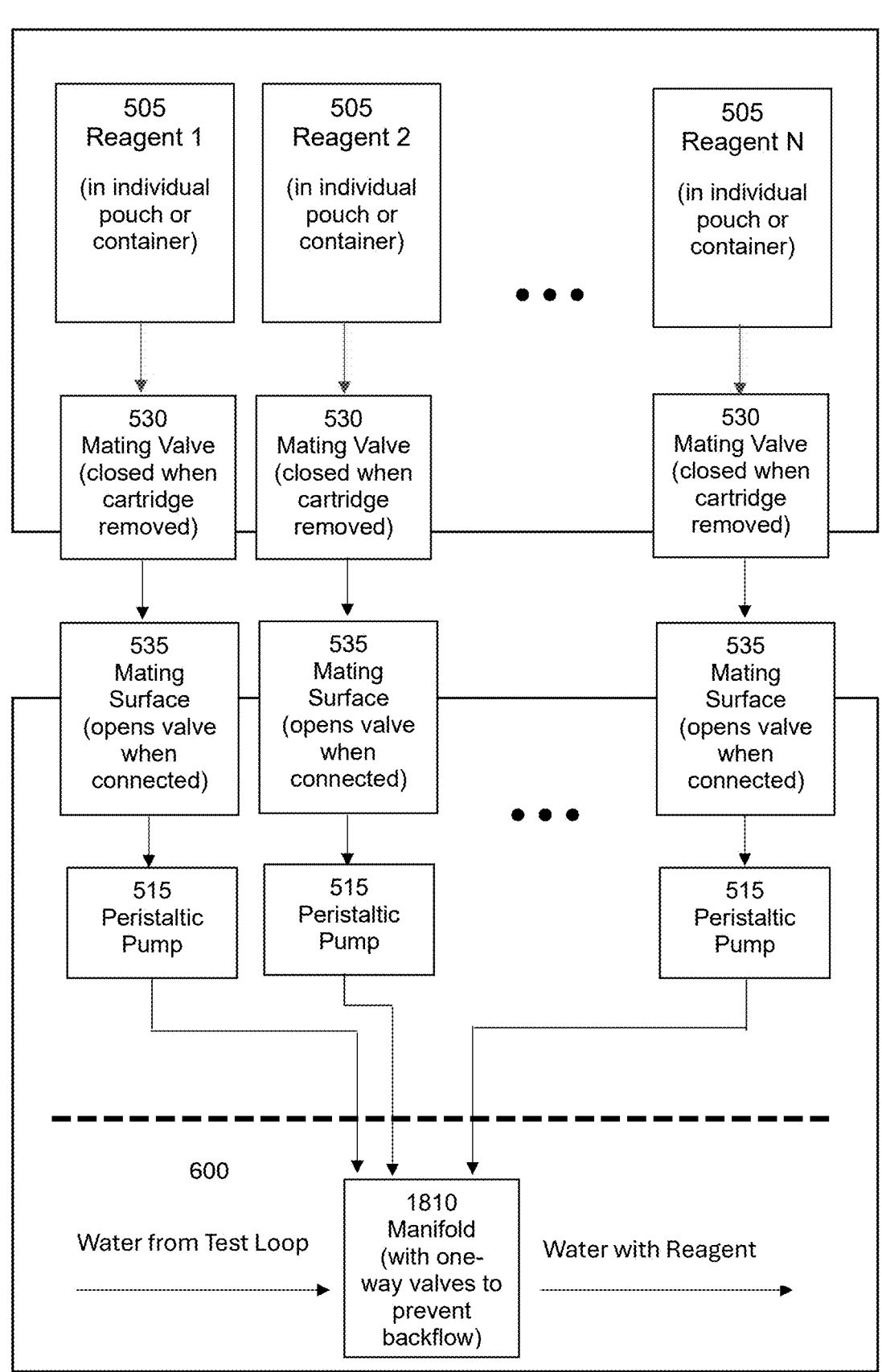
FIG. 6 is a schematic diagram of a portion of the fluid monitoring device.

FIG. 6 illustrates a schematic diagram of an important portion of the water monitoring device 100. In this block diagram, the reagent cartridge 500 has a plurality of reagent pouches 505 disposed therein. The reagent cartridge 500 includes the plurality of mating valves 530 with one valve for each of the reagent pouches 505 on the bottom of the reagent cartridge.

A mating surface 535 with the mating valve 530 is disposed within the body 110 for receiving the reagent cartridge 500. The mating valves 530 and the mating surfaces 535 are normally closed when the reagent cartridge 500 is not inserted into the body 110. However, when the reagent cartridge 500 is inserted into the body and engages the mating surface 535, the mating valves 530 and the mating surfaces 535 are all opened.

FIG. 6 also shows that each of the reagent pouches 505 are coupled, through the mating valves 530, to the plurality of individual reagent pumps 515. Each of the plurality of peristaltic reagent pumps 515 is coupled to fluid flow tubing system 555 (not shown) that incorporates or includes the circular fluid flow path 600.

More specifically, the peristaltic reagent pumps 515 are coupled to a reagent manifold 1810 that is coupled to the fluid flow tubing system 555 of the circular fluid flow path 600. The reagent manifold 1810 may include one-way valves so that backflow is prevented from going back into the reagent pouches 505.

It should be understood that the circular flow fluid path 600 describes a circular path for fluid within the fluid flow tubing system 555 that is used when a sample of water is mixed with reagents. The fluid flow tubing system 555 includes a pathway into and out of the circular flow fluid path 600 so that the combination of water and the at least one reagent can be flushed from the circular fluid flow path once mixing and measuring are performed.

When a test on water is to be performed, at least one of the peristaltic reagent pumps 515 may be activated to deliver a predetermined amount of reagent to the reagent manifold 1810. The peristaltic reagent pumps 515 may be capable of varying the amount of any reagent that is delivered because of the nature of the peristaltic pumps. That is to say, a peristaltic pump 515 may deliver small amounts of a reagent multiple times until the desired amount of a reagent is delivered.

In some examples, to run a test, a predetermined amount of test water is pulled into the circular fluid flow path 600 from a water reservoir (e.g., the test water, such as a pool). The predetermined amount of test water is simply all of the water that can fit into the test chamber 1815 (see FIG. 11A) until the test chamber is completely filled. Thus, when the testing sequence is first initiated, a predetermined amount of reagent is delivered from one or more reagent pouches 505 into the circular fluid flow path 600. The test water and reagent are then mixed.

The water-reagent mixture is then tested using a colorimeter or other sensor 725. The sensor values may be compared to a table of known values to determine the chemical levels of the test water. Other methods include mapping known values to create functions that convert raw values to chemical values, machine learning through neural networks, etc. The method for testing and monitoring water will be described in more detail below. After a test, the water-reagent mixture may be flushed from the circular fluid flow path 600 into the water reservoir.

Figure 7:
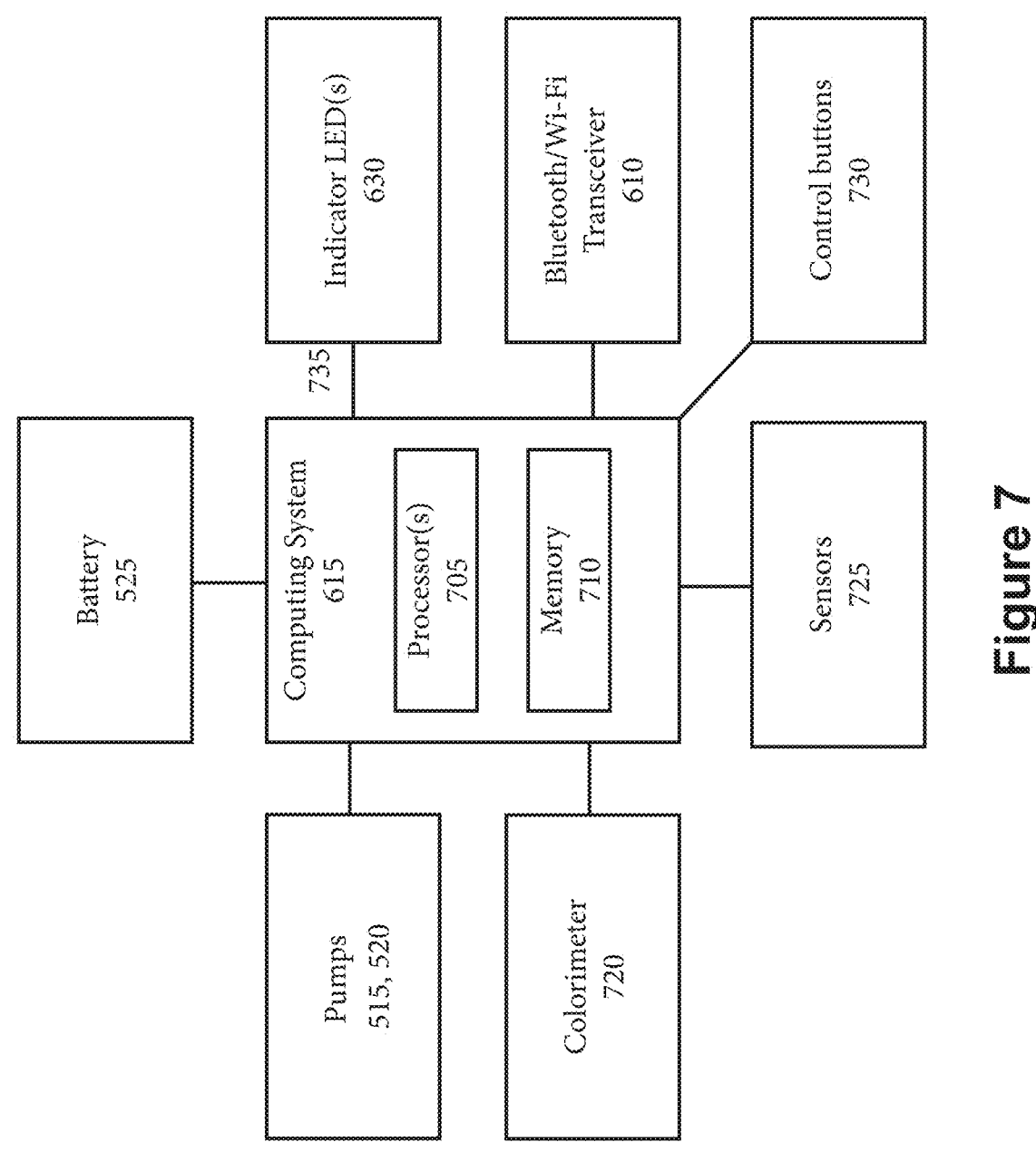
FIG. 7 illustrates an example computing system and circuitry that facilitate the operation of the fluid monitoring device.

As shown in FIG. 7, in some embodiments of the invention, the water monitoring device 100 may be comprised of a computing system 615, one or more batteries 525, and a transceiver 610. In the first embodiment, the computing system 615 may be used to run the colorimeter 720 or other sensor tests, manually or automatically, and performed periodically. For example, in the first embodiment, the water monitoring device 100 may be programmed to determine the pH levels, alkalinity levels, and chlorine levels of the test water every other day. The time between each test may vary to accommodate different needs and preferences. For example, in some examples the time between each test may be as small as a minute or be as large as desired.

Additionally, in some examples, the transceiver 610 is used to send test results to a user or database. In some examples, the test result is comprised of a color value (e.g., a RGB value or a chart of wavelength absorption), a message, and/or a recommendation. The transceiver 610 may also send messages, alerts, or other type of data/information. This may be accomplished through any kind of wired or wireless connection, including, for example, Bluetooth, Wi-Fi, GPS, or other frequency transmission capability.

For example, the results may be sent to a user's phone, smartwatch, or computer. In some examples, a user may access test results through a mobile phone app. Thus, a user may easily access information about the test water. Similarly, in the first embodiment, the water monitoring device 100 may send test results or alerts to a database through a network. For example, the database may be disposed in the Cloud or other network infrastructure. Additionally, the database may receive test results from multiple water monitoring devices 100. Thus, the database may assist a person or company to monitor many test waters.

In another example, the water monitoring device 100 sends an alert to the user and/or database. For example, a user may receive a phone notification if the test water's chemical levels are outside a predetermined range. Similarly, the database may flag all the test results that fall outside of a predetermined range. The water monitoring device 100 may also send alerts through one or more indicator LEDs 630. More specifically, the water monitoring device 100 may turn on an indicator LED 630 if the test water's chemical levels are outside a predetermined range. Another form of visible signal or audio signal may also be used.

The water monitoring device 100 may also send alerts if the device is malfunctioning or needs a reagent cartridge 500 or reagent pouch 505 replacement. For example, a user may receive a notification that states "LOW REAGENT LEVELS. REPLACE CARTRIDGE SOON." The indicator LED 630 may also alert a user of low reagent levels. For example, a yellow LED may be turned on when the reagent levels are below 30% and a red LED may be turned on when the reagent levels are below 10%.

FIG. 7 is a block diagram of the first embodiment of the computing system 615. For example, the computing system 615 is connected to the pumps 515, 520, battery 525, Bluetooth/Wi-fi Transceiver 610, Indicator LED 630, colorimeter 720, sensors 725, and control buttons 730 (not shown). Electrical wires 735 allow both electricity and data to be transferred between all the electrical components of the water monitoring device 100. It should be noted that the transceiver 610 may also use Long-Term Evolution (LTE), 5G or any other cell phone standard for communication. Additionally, in some examples, the computing system 615 does not have a battery 525. Instead, the computing system 615 is connected to a separate power source. However, in some examples, the computing system 615 has both a battery 525 and a connection to a separate power source.

Figure 8:
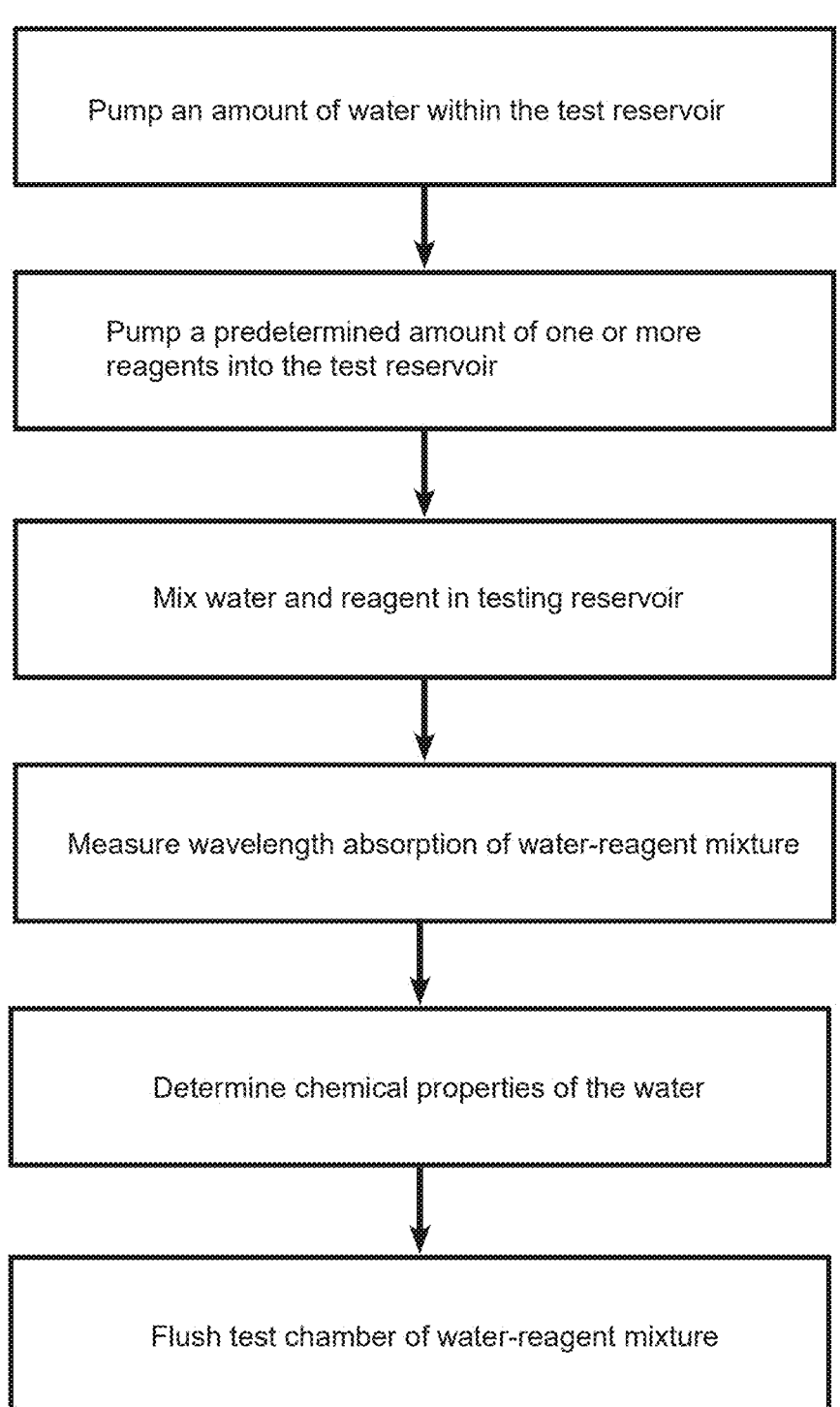
FIG. 8 illustrates an example flowchart for testing fluid using the computing system of FIG. 7 according to the principles described herein.

FIG. 8 shows an example of instructions that may be executed by the computer processor 705 and shown in the flowchart 750. The data instructions are to perform operations to test any fluid, and in particular water in this example. The system includes the computer processor 705 whereby the data instructions stored in memory 710 are executed to perform operations. The data instructions direct the mixing pump 520 to pump water into the circular fluid flow path 600 from the water reservoir. Next, the data instructions instruct the computing system 615 to direct a predetermined amount of one or more of the reagents into a test chamber 1815 from the reagent manifold 1820 within the circular fluid flow path 600. The precise operation of the test chamber 1815 will be addressed hereinafter.

The data instructions instruct the mixing pump 520 to mix the water and reagent in the circular fluid flow path 600 to create a water-reagent mixture. The data instructions then direct the colorimeter 720 to measure wavelength absorption of the water-reagent mixture. The data instructions also instruct the computing system 615 to determine the chemical properties of the water using the results of the colorimeter 720. After the test, the data instructions inform the driver to pump water into the circular fluid flow path 600 to flush the test chamber 1815 of the water-reagent mixture. In an example, the user may trigger a manual test chamber 1815 flush or the computer processor 705 may automatically trigger the test chamber flush after a predetermined amount of time or after the test results are received.

Additionally, in some examples, the water monitoring device 100 may be controlled wirelessly through Bluetooth, Wi-Fi, GPS, or other frequency transmission methods. For example, a user may manually start a water test through a phone or computer application. Similarly, a user may change the test schedule or change the test type. A user may control multiple water monitoring devices 100 at once. For example, a user may use a database to switch the schedules of all water monitoring devices 100 in a certain geographical area.

In some examples, the water monitoring device 100 is comprised of an indicator that is activated if the chemical properties of the water surpass a preselected threshold value. Thus, the user could be alerted if the chemical properties of the water are outside the desired range automatically.

Figure 9:
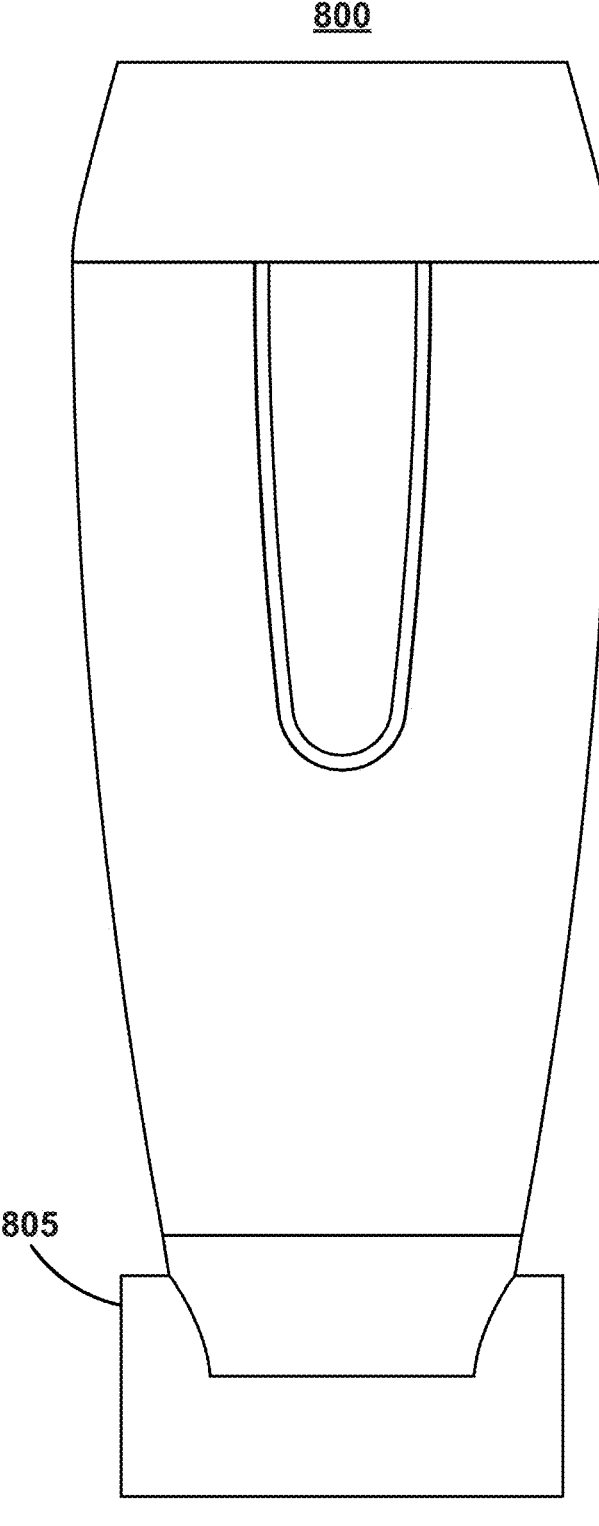
FIG. 9 illustrates a front view of an example of a fluid monitoring device that has been configured to be installed on a fluid line using a tee fitting according to principles described herein.
Figure 10:
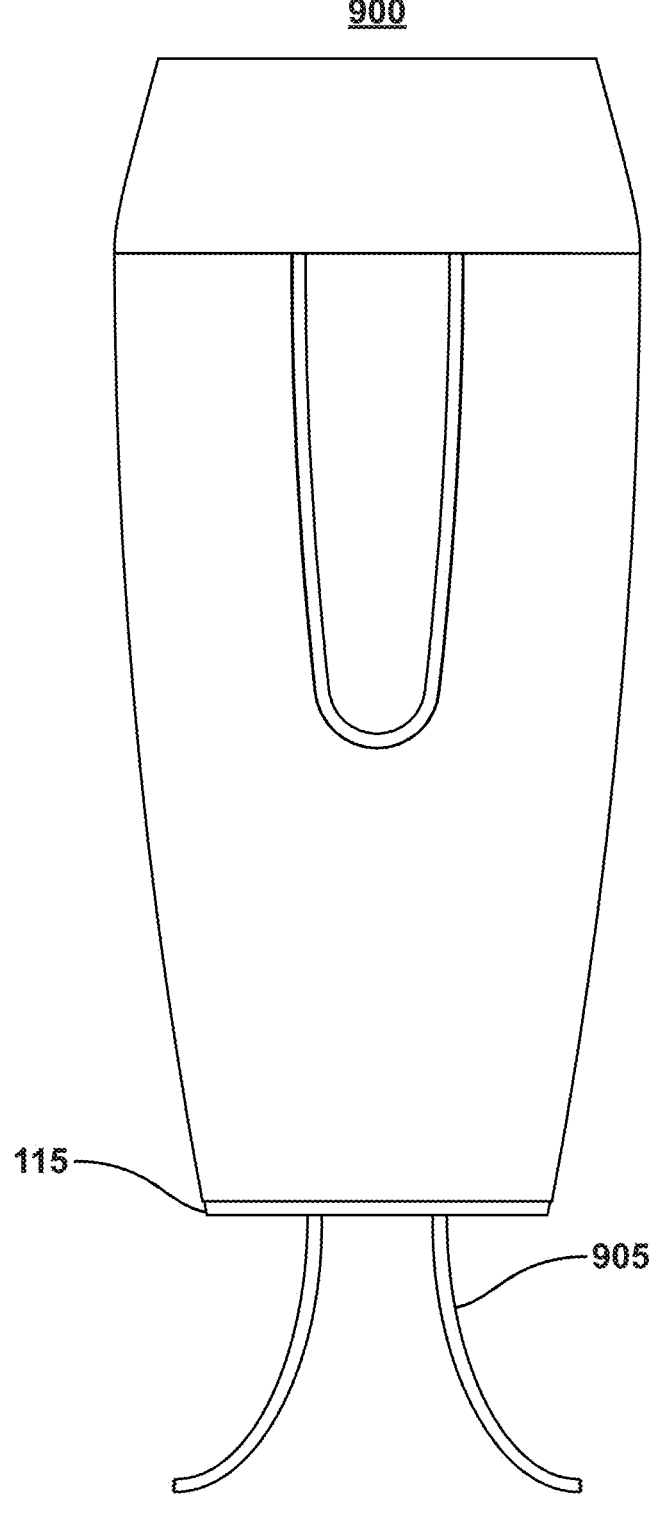
FIG. 10 illustrates a front view of an example of a fluid monitoring device that has been configured to be installed on a fluid system using flexible tubing according to the principles described herein.

FIGS. 9 and 10 illustrate water monitoring devices 800 with different attachment modules. More specifically, FIG. 9 has a tee fitting 805. The tee fitting includes a vertical flange that extends axially downward from the base of the device 800 and attaches to a first pipe and a second pipe. FIG. 10 has a flexible tube attachment 905 that includes two flexible tubes that attach at first end openings to the device and at second end openings to a water system. For example, the second end openings may attach to a pool filtering device. In some examples, the attachment module replaces the bottom cap 115. However, in other examples, the attachment module may be installed directly to the bottom cap 115.

The tee fitting 805 allows the water monitoring device 800 to be directly attached to standard-sized pipes of a water system. For example, the water monitoring device 800 may be attached to a pool's circulation line or to a pool's filtration system (e.g., a system with a filter and a circulation pump). In an example, the tee fitting 805 is used to connect the water monitoring device 800 in-line before the pool filter. In another example, the tee fitting 805 is used to connect the water monitoring device 800 in-line after the pool filter. Additionally, the size of the tee fitting may vary to accommodate different needs and preferences. For example, in some examples, the tee fitting may fit a pipe with a 1-inch nominal inside diameter or larger.

Similarly, the flexible tube attachments 905 allow the water monitoring device 900 to be easily connected to an existing water system. Additionally, the flexible tube attachment 905 allows the intake tube and the drain tube of the water monitoring device 900 to be connected to different water systems or to different sections of the same system.

In some examples, the water monitoring device 800, 900 does not use the tee fitting 805 or the flexible tube attachment 905. Instead, the water monitoring device floats in the test water and pulls/drains test water (e.g., by using a pump and/or gravity) directly from the bottom cap 115. For example, the bottom cap 115 may have an intake valve and draining valve. It should be noted that all three attachment modules provide similar functions overall. For example, all three attachment modules (e.g., the bottom cap 115, tee fitting 805, and flexible tubes 905) pull test water from the water system to the testing reservoir.

In some examples, each of the reagent pouches 505 contains a different reagent. For example, the reagent pouch 505 may contain DPD Reagent #1 (N, N-diethyl-p-phenylenediamine), DPD Reagent #2 (Monochloramine), phenol red, thiosulfate N/10, DPD reagent #3, sulfuric acid 0.12N, acid demand reagent, base demand reagent, hardness reagent, cyanuric acid reagent, and a calcium buffer. In an alternative embodiment, a reagent that is used more often or a reagent that requires larger quantities to be used than other reagents may be disposed in more than one reagent pouch 505.

Figures 11A, 11B, 11C, 11D, 11E, 11F:
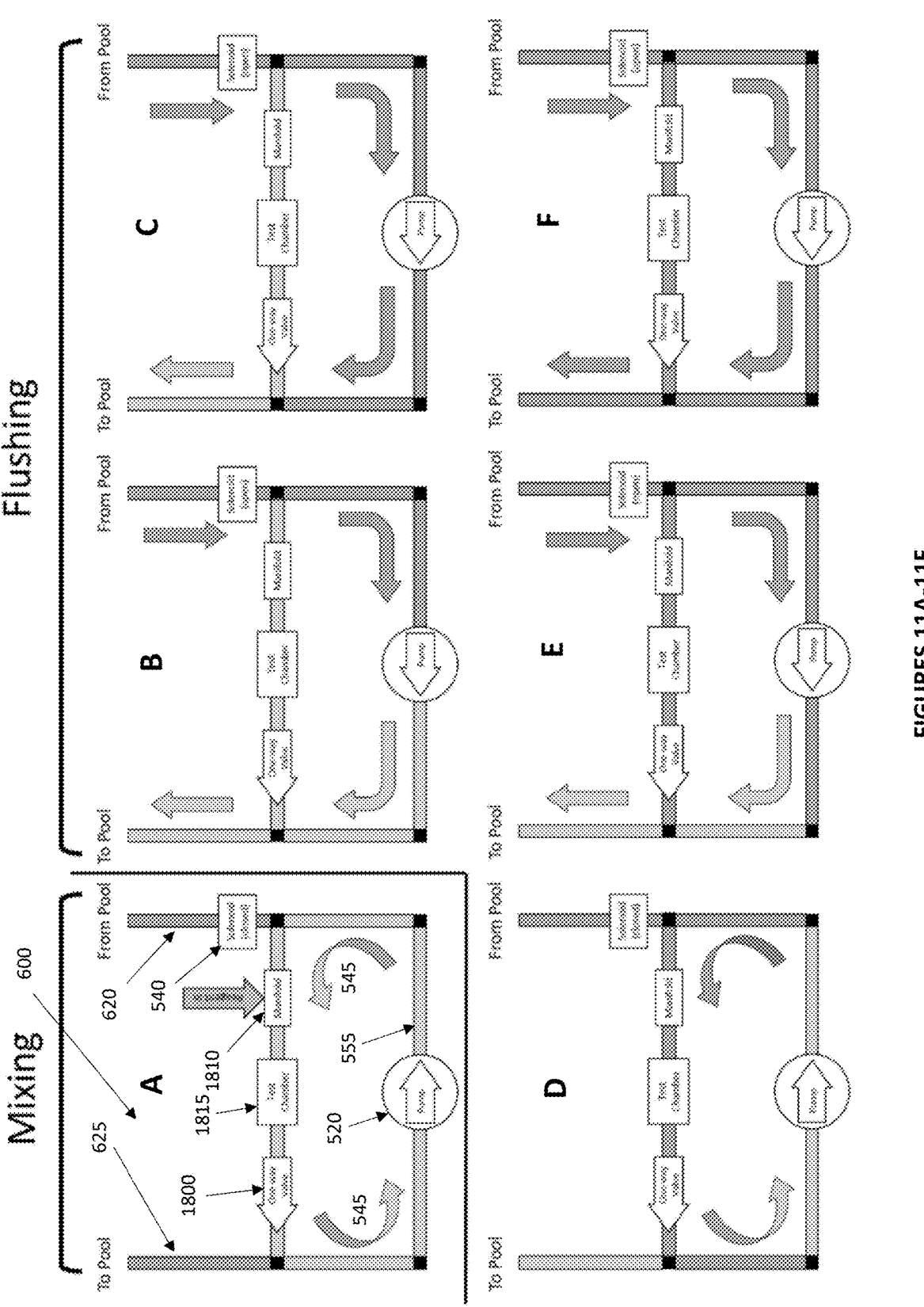
FIGS. 11A-11F illustrate the status of components in the testing reservoir when the testing reservoir has fluid ready for testing, for mixing, and for flushing from the system.

In an example of the operation of the first embodiment of the invention, FIGS. 11A-11F illustrate such an example of the optimized circular fluid flow path 600 of the present invention. As shown in FIG. 11A, the circular fluid flow path 600 is comprised of a fluid flow tubing 555, a one-way valve 1800, an intake tube 620, a drain tube 625, the mixing pump 520, a solenoid 540, the reagent manifold 1810, and a test chamber 1815. In an example, the fluid flow tubing system 555 is essentially a reservoir that may be selectively filled with water and reagents. Additionally, in some examples, the mixing pump 520 may be a peristaltic pump because of a particular advantage of a peristaltic pump. Specifically, a peristaltic pump is able to control the flow of a fluid into and out of the fluid flow tubing system 555 without having to actually seal inputs and drains.

The mixing pump 520 may also switch the flow direction. For example, in FIG. 11F the mixing pump 520 is in an initial state or first position. In some embodiments, the first position may be used to fill the circular fluid flow path 600 with test water from the intake tube 620.

Note that the one-way valve 1800 is not a powered valve but operates to allow the flow in one direction only. FIG. 11F may be thought of as an initial state of the circular fluid flow path 600 and the fluid flow tubing system 555.

In FIG. 11A, the mixing pump 520 is in a second position. In some examples, the second position may be used to mix the test water inside the circular fluid flow path 600. FIG. 11A also includes a colorimeter (not shown) in the test chamber 1815 to measure the test water's absorption of light waves. In other words, the colorimeter 720 (see FIG. 7) may determine the color of the test water inside the test chamber 1815 of the circular fluid flow path 600.

When performing a mixing operation, one or more of the reagent pumps 515 pushes reagent from one of more of the reagent pouches 500 into the reagent manifold 1810. In a first embodiment, the amount of reagent that passes through the reagent pumps 515 at any one time is a small amount, thereby allowing the reagent pumps 515 to control the quantity of reagent that is entering into the reagent manifold 1810.

As one or more of the reagent pumps 515 are pumping the reagent into the reagent manifold 1810, a solenoid 540 may be closed by the computing system 615. By closing the solenoid 540, a closed water flow path of testing water may be created within the circular fluid flow path 600. This closed water flow path is created because of the nature of the peristaltic mixing pump 520.

It should be remembered that as a peristaltic pump pushes a finite quantity of fluid through it, at the same time, it is also drawing into it the exact same amount of fluid. This is important because that means that a one-way valve is not required at the drain tube 625 to prevent water from coming back into the drain tube from the water reservoir. The mixing pump 520 is pushing out a finite amount of water and therefore must also be drawing in this exact same amount of water. Thus, the peristaltic mixing pump 520 may create a "closed" circular fluid flow path 600 as indicated by the arrows 545.

The arrows 545 therefore are an indication of the circular fluid flow path 600 within the fluid flow tubing system 555. When the circular fluid flow path 600 needs to be "closed" to perform mixing and measuring of a characteristic of the fluid and reagent mixture, the solenoid 540 is closed. This action effectively isolates the circular fluid flow path 600 as defined by arrows 545.

FIG. 11A thus shows that mixing is occurring of the test water that was already in the circular fluid flow path 600 and the one or more reagents that are being pumped into the reagent manifold 1810. The amount of time that the water-reagent mixture is sent around the circular fluid flow path 600 will be sufficient to ensure thorough mixing to create the water-reagent mixture. For example, the mixing may be performed for 60 seconds.

Once mixing is complete, the computing system 615 then performs the testing of the water-reagent mixture found in the test chamber 1815 using the colorimeter 720. In some examples, the colorimeter produces one or more test result values. In some examples, the computing system then compares the test result values against a table of known values to determine the pH levels, alkalinity levels, or chlorine levels of the test water. Additionally, in some examples, the computing system uses an equation to convert the test result values into water chemical levels (i.e., the equation produces the pH levels, alkalinity levels, or chlorine levels). In some examples, the test water's chemical levels may be stored in the computing system's memory or sent to a user's phone or computer. Furthermore, in some examples, the colorimeter determines the chemical ratio or the chemical composition of the water and reagent within the test chamber 1815. In some embodiments, the colorimeter determines the chemical values of the water (e.g., pH value, alkalinity values, and chlorine values).

After testing, the test chamber 1815 is flushed to remove all the reagents from the circular fluid flow path 600. In some examples, to flush the test chamber 1815, the direction of the mixing pump 520 must be switched several times. In an example, the direction of the mixing pump 520 switches a predetermined amount of time. In another example, the mixing pump 520 continues to switch directions until the colorimeter 720 detects chemical properties below a certain threshold. To flush the test chamber 1815, the computing system 615 makes adjustments to the solenoid 540 and to the mixing pump 520 in order to flush the water-reagent mixture from the testing reservoir in preparation for a subsequent test.

FIG. 11B shows that the solenoid 540 is changed from closed to open and the direction of the mixing pump 520 changes from the second position shown in FIG. 11A to the first position shown in FIG. 11B. As the mixing pump 520 starts operating, because of the position of the one-way valve 1800, clean test water is drawn in from the water reservoir through the intake tube 620. As shown, the clean test water is not flowing through the test chamber 1815 yet but is flowing through a lower reservoir path.

FIG. 11C shows that the clean test water has now passed through the mixing pump 520 and cleaned the lower reservoir path.

FIG. 11D shows that the computing system 615 then closes the solenoid 540 and the mixing pump 520 is changed from the first position to the second position. Clean test water is now drawn from the lower circular fluid flow path and through the upper circular fluid flow path through the test chamber 1815.

FIG. 11E shows that the computing system 615 then opens the solenoid 540 and the mixing pump 520 is changed from the second position to the first position allowing clean test water to again enter into the circular fluid flow path 600 and push out the remaining water-reagent mixture out of the drain tube 625 as shown in FIG. 11F.

The process is then repeated in FIGS. 11B to 11F until all the water-reagent mixture has been removed from the circular fluid flow path 600. In some examples, the process may be repeated four or more times to flush the system. However, other examples may flush the system with four or less cycles. The circular fluid flow path 600 is then again in a beginning state shown in FIG. 11F and ready for more testing to proceed.

One of the main advantages of the first embodiment of the invention shown above is that the circular fluid flow path 600 requires less power to operate, is less complex, and includes fewer moving parts than the prior art. It is suggested that a substantial decrease in power requirements enables the water testing system 100 to operate far longer between recharging because less power is needed to clean the circular fluid flow path 600. The first embodiment only requires that the solenoid 540 be opened and closed, and that a single mixing pump 520 be operated to perform mixing of the water-reagent mixture as well as flushing and cleaning of the circular fluid flow path 600.

Furthermore, because of the use of fewer moving parts than systems of the prior art, the water testing system 100 is less prone to failure and thus the need for repairs or replacement may be substantially reduced.

Having described the components and operation of the first embodiment in detail, a second embodiment of the invention is also presented herein to show further improvements.

Specifically, while the first embodiment decreased the complexity of the circular fluid flow path 500, the second embodiment may be a further refinement by eliminating the one-way valve 1800 and the solenoid 540 shown in FIGS. 11A-11F.

Figures 12A, 12B:
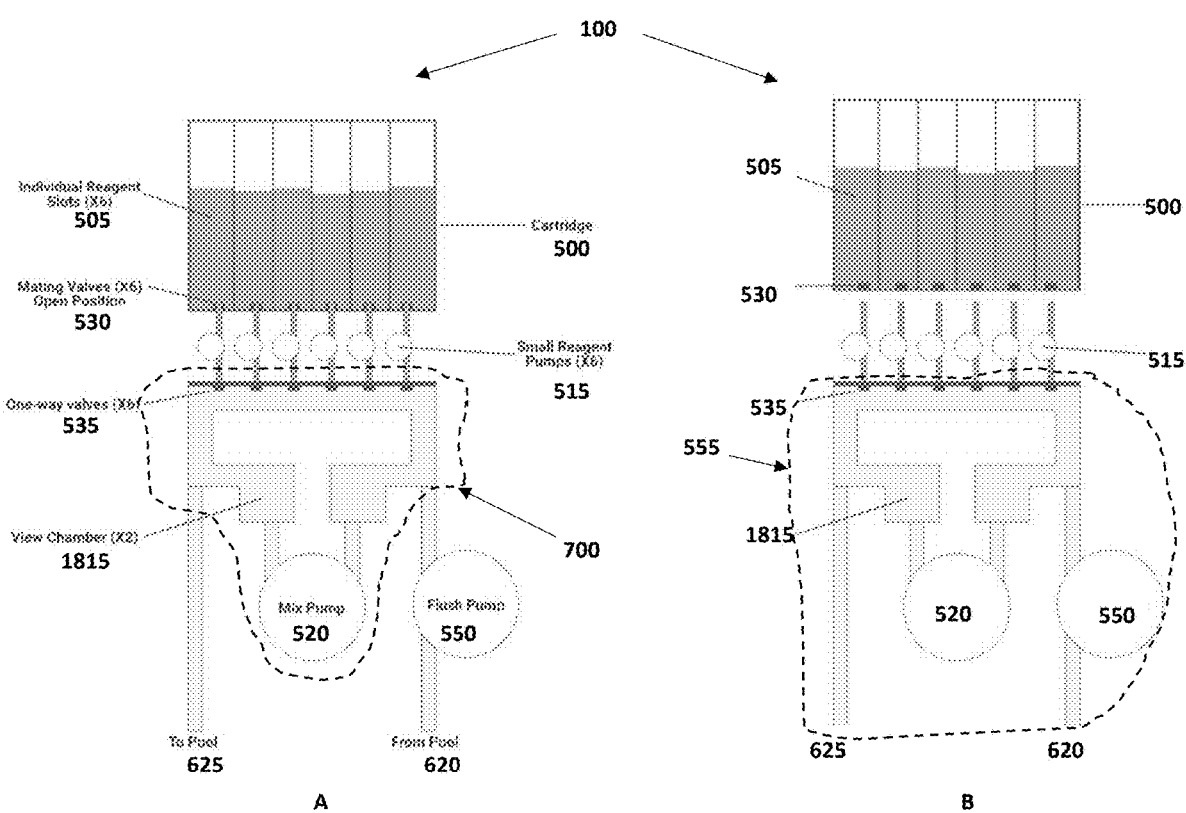
FIGS. 12A and 12B illustrate a circular fluid flow path of the second embodiment.

FIGS. 12A and 12B show a circular fluid flow path 700 of the second embodiment that has some important differences from the circular fluid flow path 600 of the first embodiment. More specifically, the figures show a block diagram of major components of the second embodiment of the water monitoring device 100 of the present invention. These components include the reagent cartridge 500, the plurality of reagent slots 505, the plurality of mating valves 530, a plurality of peristaltic reagent pumps 515, one for each of the plurality of reagent slots, and a pump valve 535 having a plurality of openings, one opening for each of the peristaltic reagent pumps. The one-way pump valves 535 lead to the fluid flow tubing system 555 as shown in FIG. 12B. The components also include a test chamber 1815, an intake tube 620, a drain tube 625, a peristaltic mixing pump 520 and an additional peristaltic flush pump 550 that is not found in the first embodiment. The addition of the flush pump 550 enables the second embodiment to eliminate the one-way valve 1800 and the solenoid 540 shown in FIGS. 11A-11F.

It is also noted that by attaching each of the plurality of pump valves 535 directly to the fluid flow tubing 555, the manifold 1810 may also be eliminated.

In an example of the operation of the second embodiment of the invention, FIGS. 13A-13F illustrate such an example of the optimized circular fluid flow path 700 of the present invention. First, it is noted that FIG. 12B illustrates that the reagent cartridge 500 has not been coupled to the plurality of reagent pumps 515. In contrast, FIG. 12A shows that the reagent cartridge 500 has been coupled to the plurality of reagent pumps 515, thereby opening the plurality of mating valves 530. The plurality of mating valves 530 may remain open because none of the reagent in the reagent cartridge 500 can enter into the circular fluid flow path 700 until one of the plurality of reagent pumps 515 is activated.

Figures 13A, 13B, 13C, 13D, 13E, 13F:
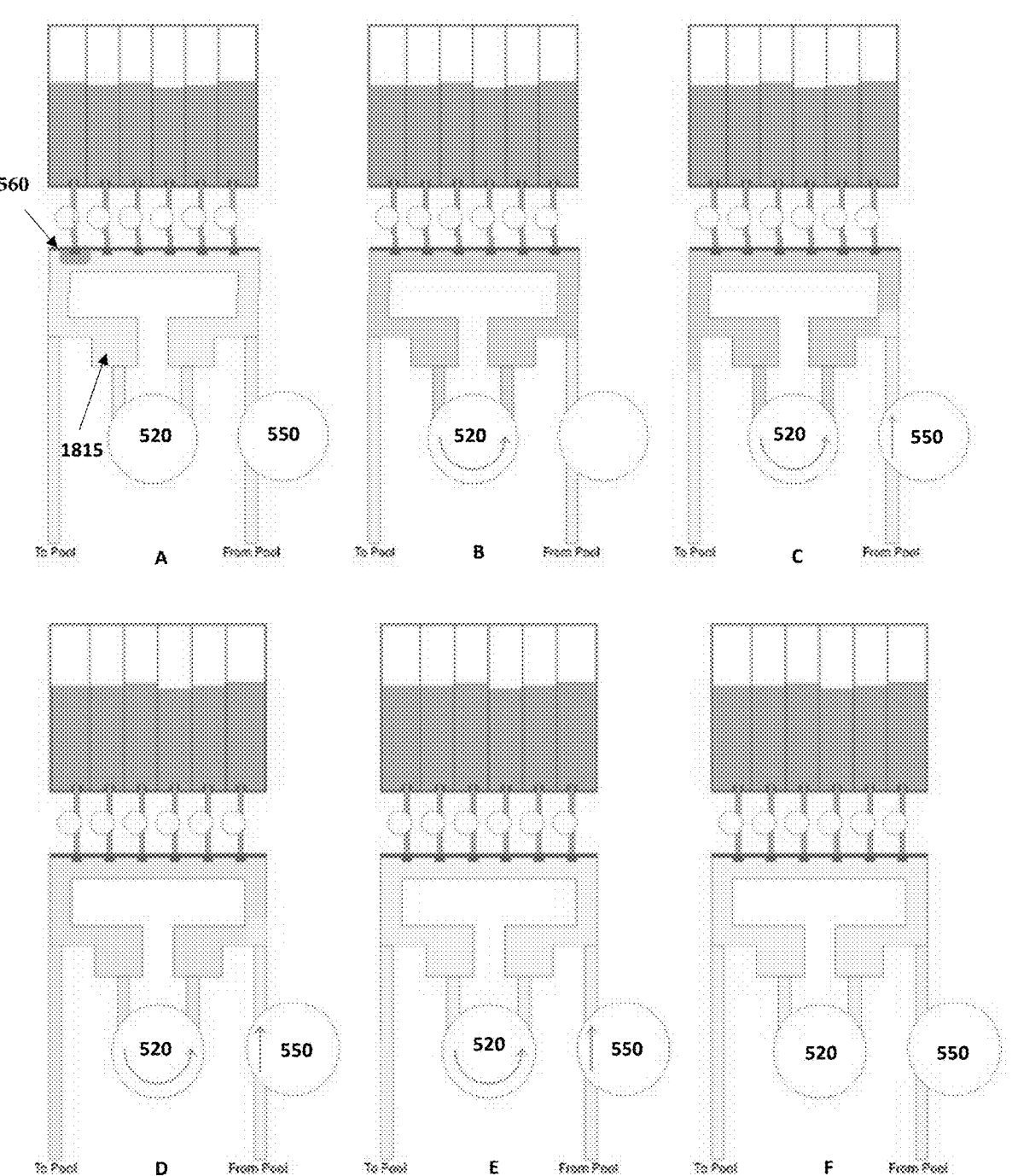
FIGS. 13A-13F illustrate the process of adding a reagent to a fluid sample to be tested, and the process for flushing the sample once the measurement is taken.

FIG. 13A shows that some reagent has entered the circular fluid flow path 700 because of activation of one of the plurality of reagent pumps 515. It is assumed that the water in the circular fluid flow path 700 is a test sample that has no reagent disposed therein.

FIG. 13B shows that the mixing pump 520 is activated in a single direction that is indicated by an arrow, and thereby causing a counterclockwise flow of water through the circular fluid flow path 700. It is noted that none of the water and reagent mixture will pass out of the drain tube 625 and no fresh sample water will enter through the intake tube 620 because the peristaltic mixing pump 520 only allows the exact same amount of water to flow through the circular fluid flow path 700 that is already present.

Figure 14:
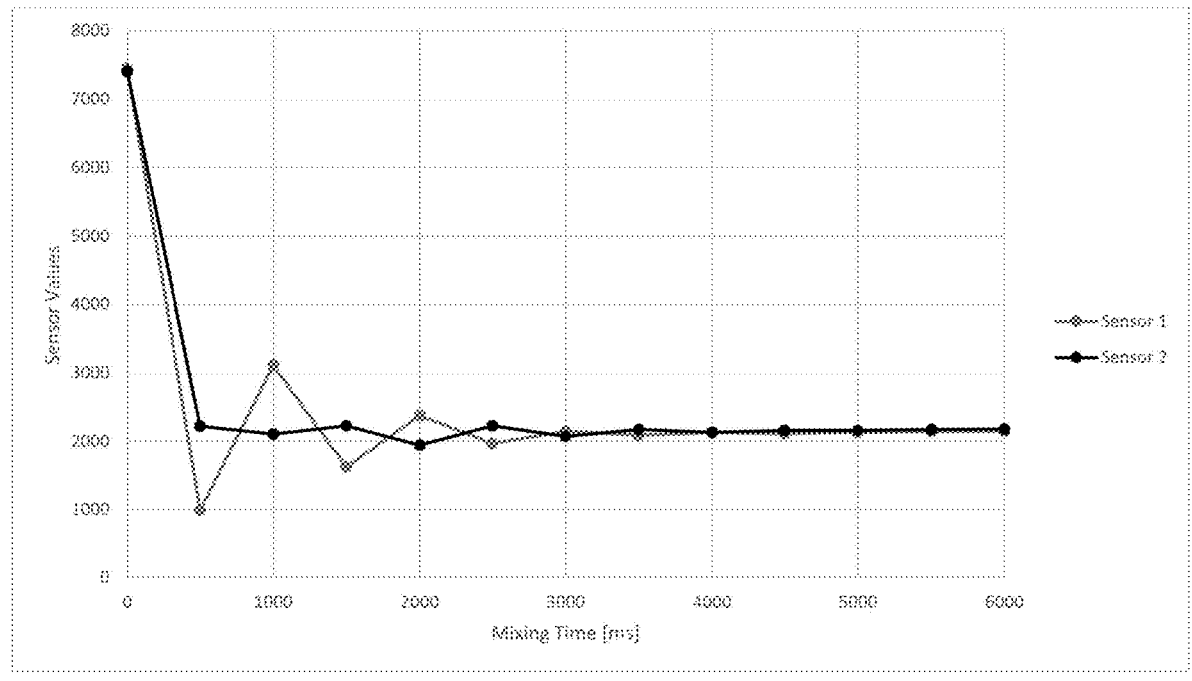
FIG. 14 is a graph showing how long it takes to mix the water and reagent in the fluid testing device using the second embodiment of the invention.

FIG. 14 is a graph that illustrates that unlike the first embodiment which may take up to 60 seconds to mix the water and the reagent in the circular fluid flow path 700, the second embodiment only requires four to five seconds for an adequate mixing of the water-reagent mixture to occur to be ready for a measurement.

Accordingly, the measurement of the water-reagent mixture is then taken after the mixing of the water and the reagent shown in FIG. 13B. After the measurement has been taken using a sensor in the test chamber 1815, the mixture needs to be flushed from the circular fluid flow path 700.

FIG. 13C shows that flushing the mixture from the circular fluid flow path 700 may be accomplished by continuing to operate the mixing pump 520 but also activating the flushing pump 550 by drawing water in from the intake tube 620. Operating both the mixing pump 520 and the flushing pump 550 at the same time will cause water to be drawn into the circular fluid flow path 700 and directed out the drain tube 625. The operation of the pumps 520, 550 continues until sufficient water has been drawn into the circular fluid flow path 700 as well as directed out the drain tube 625 as shown in FIGS. 13D and 13E. The pumps 520, 550 are then deactivated as shown in FIG. 13F when the circular fluid flow path 700 has a sufficiently clean test sample of water in the circular fluid flow path.

Figure 15:
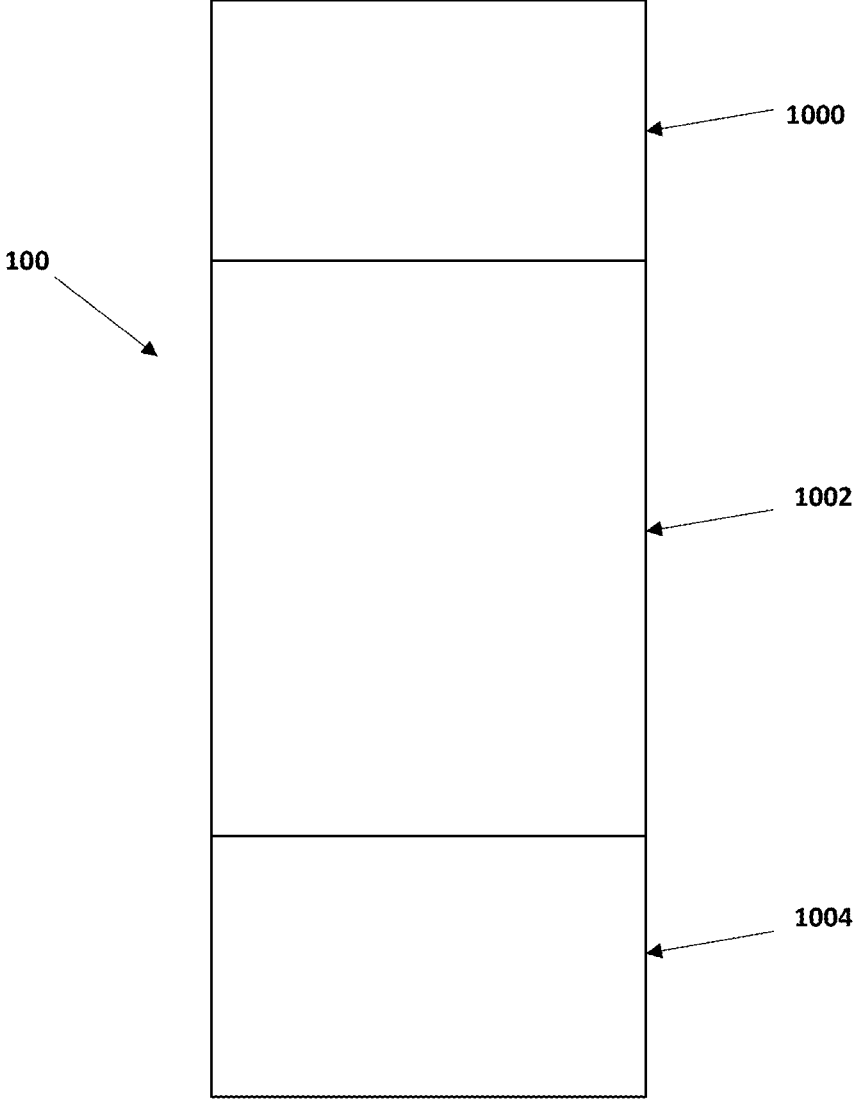
FIG. 15 is a block diagram of modularized components in another embodiment of a water quality testing system.

In a step to increase modularity of the fluid testing device and thereby simplify operation, FIG. 15 shows in a block diagram the components of the fluid testing device in another embodiment of the invention. FIG. 15 shows that the components of the water monitoring device 100 now include a reagent cartridge module 1000, a testing module 1002, and a connection module 1004.

The connection module 1004 may include such attachments as an in-line coupler to enable the water monitoring device 100 to be coupled into an existing water system. The connection module 1004 may also include an in-fluid float model, a rigid pipe in-line module, a flexible pipe in-line module, and a tabletop off-line module.

Figure 16:
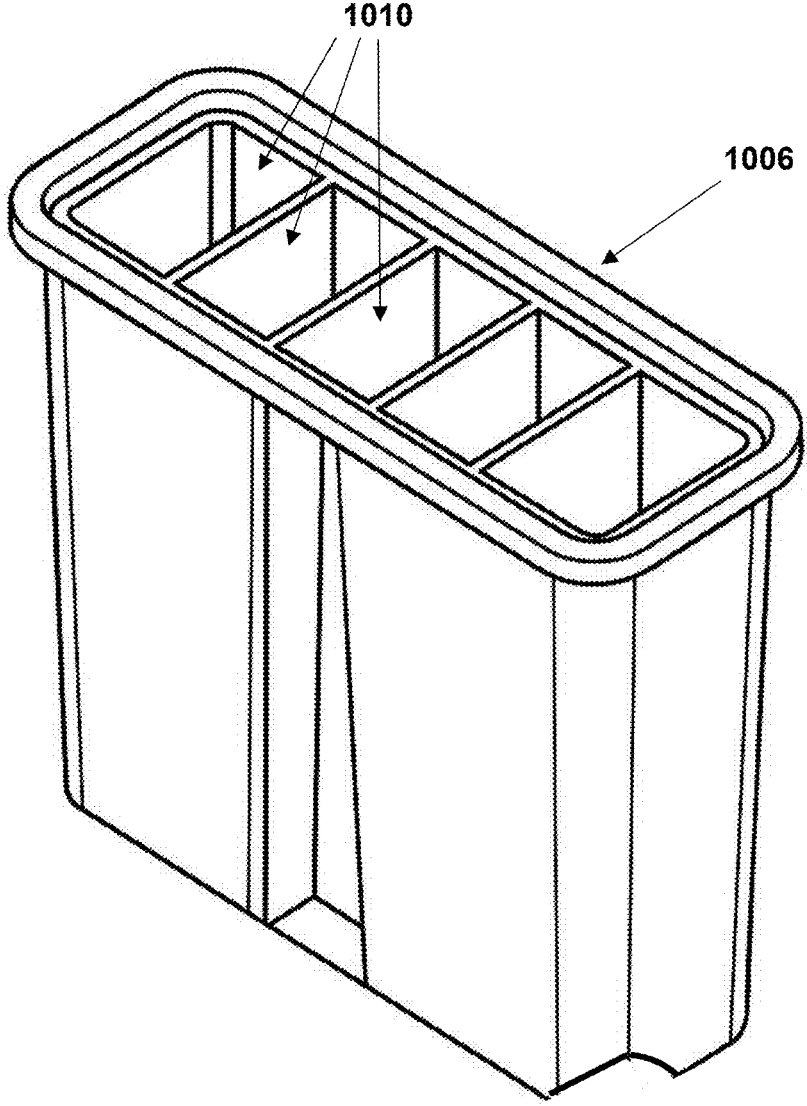
FIG. 16 is a perspective illustration of a modular reagent cartridge that is divided into separate compartments for the various reagents.

The cartridge module 1000 may not use reagent pouches but instead uses a modular and replaceable reagent cartridge 1006 that may contain all of the reagents in a single cartridge, wherein the module is divided into separate reagent compartments (slots) 1008 for the various reagents as shown in FIG. 16. The separate reagent compartments 1008 may be of different dimensions so that reagents used more often or used in greater volume may have more storage space.

Figure 17:
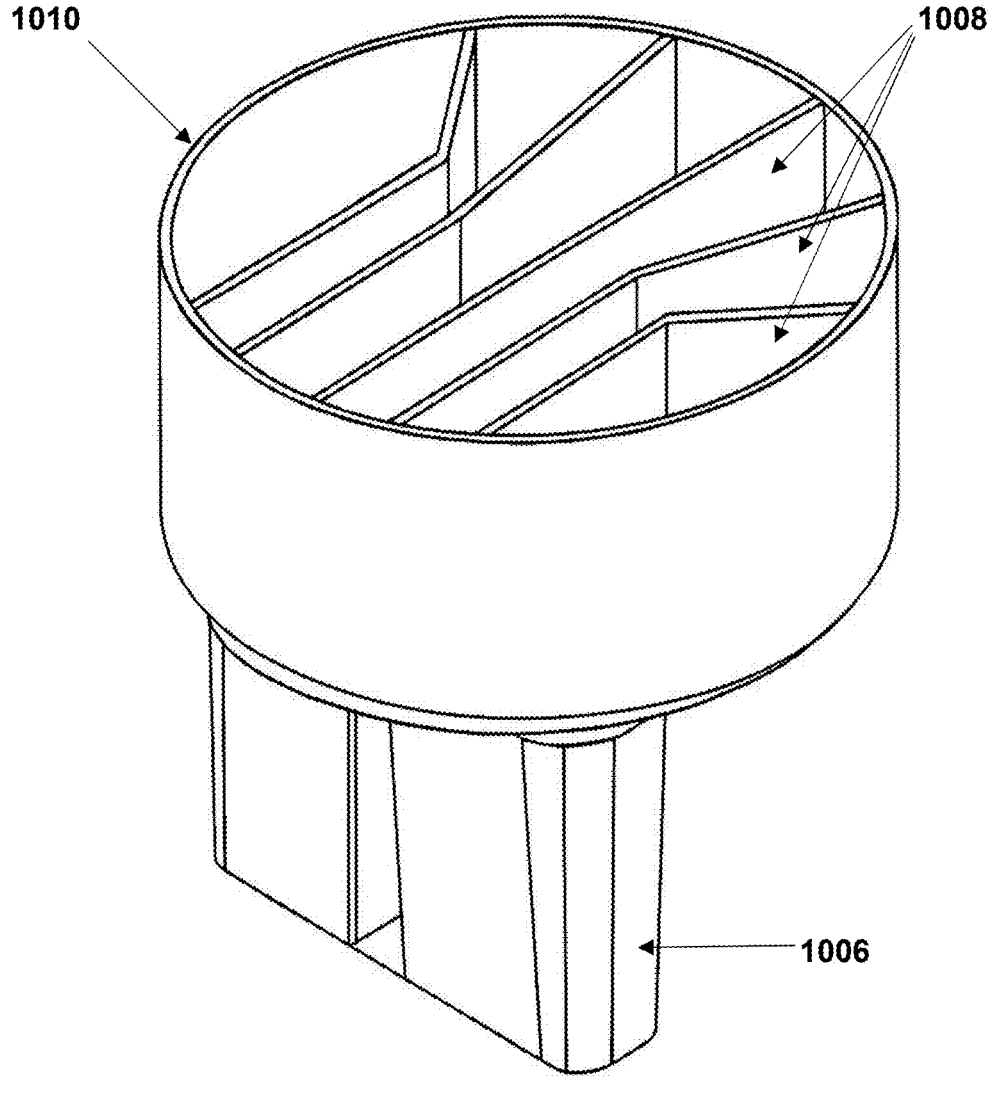
FIG. 17 is a perspective illustration of the modular reagent cartridge having a reagent expander disposed on top of the modular reagent cartridge in order to increased cartridge capacity.

In this alternative embodiment, the cartridge module 1000 may also be expandable. As shown in FIG. 17, the modular reagent cartridge 1006 may have a reagent expander 1010 disposed on top of the modular reagent cartridge, and thereby expanding the amount of reagents that are storable in the cartridge module 1000.

Figure 18:
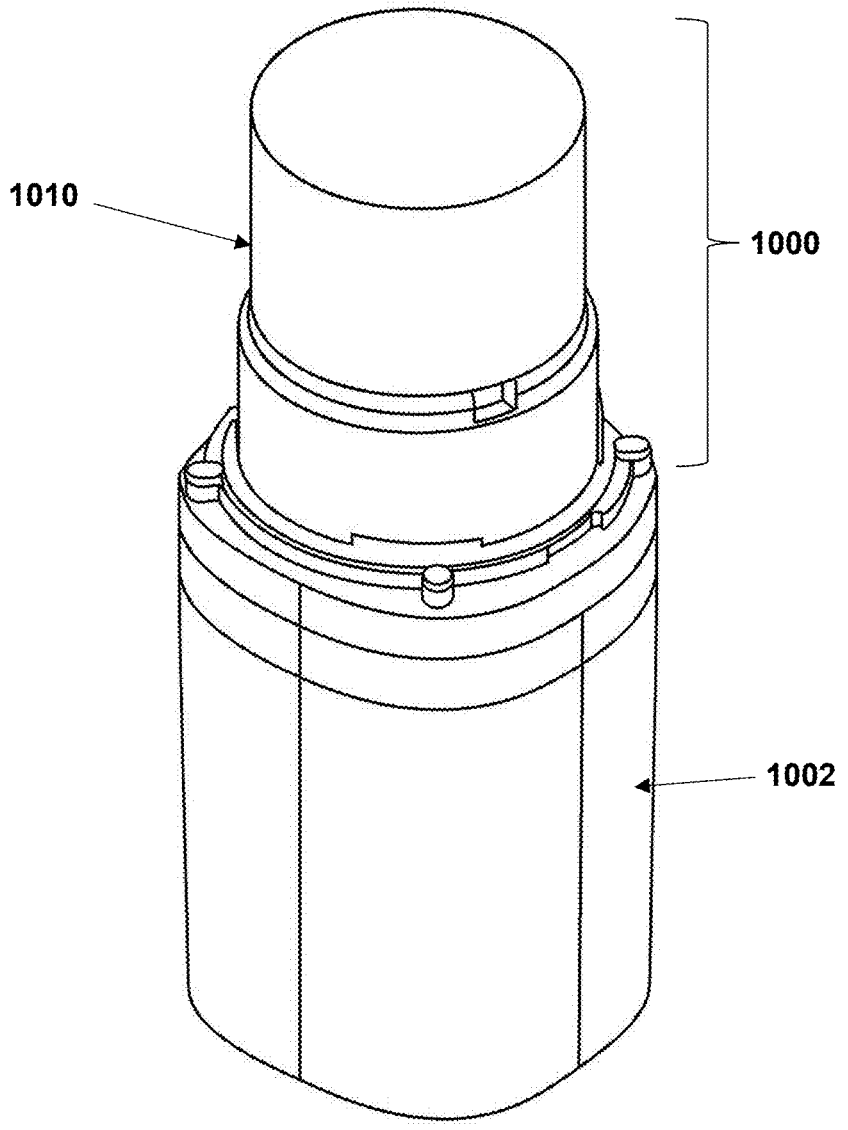
FIG. 18 is a perspective view of the reagent expander with a cover on it and disposed on the housing.

FIG. 18 is a perspective view of the reagent expander 1010 with a cover on it and disposed on the cartridge module 1000.

The invention may be summarized as a method for minimizing power consumption and reducing complexity of a fluid monitoring device, said method comprising the steps of 1) providing a reagent cartridge having a plurality of reagent slots or containers, a plurality of reagent pumps, one for each of the plurality of reagent slots or containers, a fluid flow tubing coupled to the plurality of reagent pumps for receiving at least one reagent therefrom, a test chamber for receiving a mixture of a fluid and the at least one reagent, and for measuring at least one characteristic of the mixture of the fluid and the at least one reagent, and a circular fluid flow path that includes the test chamber and a peristaltic mixing pump 2) delivering a desired amount of at least one reagent from the plurality of reagent pouches to the fluid flow tubing using at least one of the plurality of reagent pumps, 3) activating the peristaltic mixing pump, 4) mixing the at least one reagent and the fluid together within the circular fluid flow path of the fluid flow tubing, 5) deactivating the peristaltic mixing pump, and 6) measuring the at least one characteristic of the mixture of the fluid and the at least one reagent in the test chamber.

In a different embodiment, a method of using the first embodiment of the invention may proceed as follows. The first embodiment is a method for minimizing power consumption and reducing the complexity of a fluid monitoring device, said method comprising the steps of: 1) providing a reagent cartridge having a plurality of reagent pouches, a plurality of reagent pumps, one for each of the plurality of reagent pouches, a manifold coupled to the plurality of reagent pumps for receiving at least one reagent therefrom, a test chamber for receiving a mixture of a fluid and the at least one reagent, and for measuring at least one characteristic of the mixture of the fluid and the at least one reagent, and a circular fluid flow path that includes in series a solenoid, the manifold, the test chamber, a one-way valve, and a peristaltic mixing pump that leads back to the solenoid, 2) delivering a desired amount of at least one reagent from the plurality of reagent pouches to the manifold using at least one of the plurality of reagent pumps, 3) inserting the at least one reagent into a fluid in the circular fluid flow path, 4) closing the solenoid, 5) activating the peristaltic mixing pump to pump toward the solenoid until the at least one reagent and the fluid are mixed together within the circular fluid flow path, 6) deactivating the peristaltic mixing pump, and 7) measuring the at least one characteristic of the mixture of the fluid and the at least one reagent in the test chamber.

The next step is to flush the mixture of the at least one reagent and the fluid from the circular fluid flow path to prepare for a new measurement. This may be accomplished by the steps of 1) opening the solenoid, reversing direction of the peristaltic mixing pump, and activating the peristaltic mixing pump until untested fluid flows in through the inlet tube until it reaches a junction between the one-way valve and the drain tube, 2) closing the solenoid, reversing direction of the peristaltic mixing pump, and activating the peristaltic mixing pump until untested fluid passes through the one-way valve, and 3) opening the solenoid, reversing direction of the peristaltic mixing pump, and activating the peristaltic mixing pump until untested fluid passes the junction between the one-way valve and the drain tube.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A fluid monitoring device configured for testing a fluid and having an optimized circular fluid flow path to minimize power consumption, said fluid monitoring device comprised of:

a reagent cartridge having a plurality of reagent compartments;

a plurality of reagent pumps, one for each of the plurality of reagent compartments;

a circular fluid flow path coupled to each of the plurality of reagent pumps;

a test chamber disposed in the circular fluid flow path; and a peristaltic mixing pump disposed in the circular fluid flow path;

wherein the circular fluid flow path receives at least one reagent from at least one of the plurality of reagent pumps into the fluid in the circular fluid flow path, closing the circular fluid flow path, activating the peristaltic mixing pump, mixing the at least one reagent with the fluid in the circular fluid flow path by pumping the at least one reagent with the fluid through the closed circuit fluid flow path, deactivating the peristaltic mixing pump, and measuring at least one characteristic of the fluid and the at least one reagent in the test chamber.

2. The fluid monitoring device as defined in claim 1, wherein the circular fluid flow path is further comprised of:

an intake tube configured for receiving the fluid from a fluid source, a peristaltic flush pump disposed in the intake tube; and a drain tube configured for draining the mixture of the fluid and the at least one reagent.

3. The fluid monitoring device as defined in claim 2, wherein the test chamber is further comprised of a sensor configured for measuring the at least one characteristic of the mixture of the fluid and the at least one reagent.

4. The fluid monitoring device as defined in claim 3, wherein the sensor is further comprised of a colorimeter configured for measuring the absorption of light waves in the mixture of the fluid and the at least one reagent.

5. The fluid monitoring device as defined in claim 1, wherein the fluid monitoring device is further comprised of:

a computing system configured for controlling operation of the fluid monitoring device;

a transceiver configured for sending and receiving data from the fluid monitoring device;

at least one external control button configured for operating the fluid monitoring device; and a battery configured for providing power to the fluid monitoring device.

6. The fluid monitoring device as defined in claim 1, wherein the fluid monitoring device is further comprised of a plurality of reagent cartridge valves disposed between the reagent cartridge and the plurality of reagent pumps, wherein the plurality of cartridge valves are normally closed until the reagent cartridge is inserted into and coupled to the fluid monitoring device.

7. The fluid monitoring device as defined in claim 6, wherein the fluid monitoring device is further comprised of a plurality of pump valves disposed between the plurality of reagent pumps and the circular fluid flow path.

8. The fluid monitoring device as defined in claim 1, wherein the fluid monitoring device is a battery powered water monitoring and testing system that floats on a body of water and performs periodic testing of the water.

9. The fluid monitoring device as defined in claim 1, wherein the plurality of reagent pumps are comprised of a plurality of peristaltic pumps that enable delivery of discrete units of reagents into the circular fluid flow path.

10. A method for minimizing power consumption of a fluid monitoring device, said method comprising:

providing a reagent cartridge having a plurality of reagent compartments, a plurality of reagent pumps, one for each of the plurality of reagent compartments, a circular fluid flow path coupled to each of the plurality of reagent pumps, a test chamber disposed in the circular fluid flow path, and a peristaltic mixing pump disposed in the circular fluid flow path;

delivering a desired amount of at least one reagent from the plurality of reagent compartments to the circular fluid flow path using at least one of the plurality of reagent pumps;

closing the circular fluid flow path;

activating the peristaltic mixing pump to mix the at least one reagent with the fluid in the circular fluid flow path by pumping the at least one reagent with the fluid through the closed circular fluid flow path for a period of time;

deactivating the peristaltic mixing pump; and measuring the at least one characteristic of the fluid and the at least one reagent in the test chamber.

11. The method as defined in claim 10, wherein the method further comprises flushing the mixture of the at least one reagent and the fluid from the circular fluid flow path to prepare for a new measurement.

12. The method as defined in claim 11, wherein the step of flushing a mixture of the at least one reagent and the fluid from the circular fluid flow path further comprises:

providing an intake tube configured for receiving the fluid from a fluid source, a peristaltic flush pump disposed in the intake tube, and a drain tube configured for draining the mixture of the fluid and the at least one reagent; and activating both the peristaltic flush pump and the peristaltic mixing pump to thereby draw fluid into the circular fluid flow path from the intake tube and causing the fluid to flow out of the drain tube.

13. The method as defined in claim 10, wherein the step of measuring the at least one characteristic of the mixture of the fluid and the at least one reagent in the test chamber further comprises:

activating a colorimeter; and measuring the absorption of light waves in the mixture of the fluid and the at least one reagent.

14. The method as defined in claim 10, wherein the method further comprises providing a computing system configured for controlling operation of the fluid monitoring device, providing a transceiver configured for sending and receiving data from the fluid monitoring device, providing at least one external control button configured for operating the fluid monitoring device, and providing a battery configured for supplying power to the fluid monitoring device.

15. A fluid monitoring device for testing a fluid and having an optimized circular fluid flow path to minimize power consumption, said fluid monitoring device comprised of:

a reagent cartridge having a plurality of reagent pouches;

a plurality of reagent pumps, one for each of the plurality of reagent pouches;

a manifold coupled to the plurality of reagent pumps configured for receiving at least one reagent therefrom;

a test chamber configured for receiving a mixture of a fluid and the at least one reagent, and for measuring at least one characteristic of the mixture of the fluid and the at least one reagent; and a circular fluid flow path that includes in series a solenoid, the manifold, the test chamber, a one-way valve, and a peristaltic mixing pump that leads back to the solenoid, wherein the circular fluid flow path receives the at least one reagent from the manifold, the circular fluid flow path is closed, the peristaltic mixing pump is activated for a period of time, mixing the at least one reagent with the fluid in the circular fluid flow path by pumping the at least one reagent with the fluid through the closed circuit fluid flow path, deactivating the peristaltic mixing pump, and measuring at least one characteristic of the fluid and the at least one reagent, and then flushing the fluid and the at least one reagent from the circular fluid flow path to prepare for a new measurement.

16. A method for minimizing power consumption of a fluid monitoring device by optimizing a system for mixing, testing and flushing fluid and reagent from the fluid monitoring device, said method comprising:

providing a circular fluid flow path that includes in series a solenoid, a manifold, a test chamber, a one-way valve, and a peristaltic mixing pump that leads back to the solenoid;

delivering a desired amount of at least one reagent to the manifold;

inserting the at least one reagent into a fluid in the circular fluid flow path from the manifold;

closing the solenoid to thereby close the circular fluid flow path;

activating the peristaltic mixing pump to pump toward the solenoid until the at least one reagent and the fluid are mixed together within the circular fluid flow path for a period of time;

deactivating the peristaltic mixing pump; and measuring the at least one characteristic of the mixture of the fluid and the at least one reagent in the test chamber.

17. The method as defined in claim 16, wherein the method further comprises flushing the mixture of the at least one reagent and the fluid from the circular fluid flow path to prepare for a new measurement.

18. The method as defined in claim 17, wherein the step of flushing the mixture of the at least one reagent and the fluid from the circular fluid flow path further comprises:

providing an intake tube from a fluid source, wherein the intake tube is coupled to the fluid flow circuit at the solenoid, and a drain tube coupled to the circular fluid flow path between the one-way valve and the peristaltic mixing pump;

activating and deactivating the solenoid in the circular
fluid flow path to control a flow of untested fluid into
the circular fluid flow path; and
changing direction of the peristaltic mixing pump more
than once so that the pump draws untested fluid into the
circular fluid flow path and expels fluid that is mixed
with the at least one reagent out through the drain tube.

\* \* \* \* \*